US005936084A

United States Patent [19]

[11] Patent Number: 5,936,084

[45] Date of Patent: Aug. 10, 1999

Jirousek et al.

[54] HALO-SUBSTITUTED BISINDOLEMALEIMIDE PROTEIN KINASE C INHIBITORS

[75] Inventors: Michael R. Jirousek, Hamburg, Germany; Peter G. Goekjian; Guo-Zhang Wu, both of Starkville, Miss.

[73] Assignees: Eli Lilly and Company, Indianapolis, Ind.; Mississippi State University, Mississippi State, Miss.

[21] Appl. No.: 08/846,272

[22] Filed: Apr. 30, 1997

Related U.S. Application Data

[60] Provisional application No. 60/016,382, May 1, 1996.

[51] Int. Cl.$^{6}$ ...................... C07D 269/00; C07D 413/14; A61K 31/55; A61K 31/395

[52] U.S. Cl. .......................... 540/454; 514/183; 514/185; 514/410; 540/450; 540/456; 540/467; 540/472; 640/480; 640/474

[58] Field of Search .................................... 540/454, 467, 540/472, 480, 456, 450, 474; 514/183, 185, 410

[56] References Cited

U.S. PATENT DOCUMENTS

| | | | |
|---|---|---|---|
| 5,380,746 | 1/1995 | Barth et al. | 514/414 |
| 5,438,050 | 8/1995 | Kleinschroth et al. | 514/183 |
| 5,516,915 | 5/1996 | Barth et al. | 548/455 |
| 5,552,396 | 9/1996 | Heath et al. | 514/183 |
| 5,559,228 | 9/1996 | Heath et al. | 540/460 |
| 5,589,472 | 12/1996 | Vice | 514/183 |
| 5,621,098 | 4/1997 | Heath, Jr. et al. | 540/472 |
| 5,624,108 | 4/1997 | Heath et al. | 514/410 |
| 5,696,949 | 12/1997 | Heath et al. | 514/183 |

OTHER PUBLICATIONS

"A Short Synthesis of 2–Deoxy–2–fluoro–ribo–D–pentopyranose", Welch et al., J. Chem. Soc., Chem. Commun., pp. 186–188, 1985.

*Primary Examiner*—Floyd D. Higel
*Attorney, Agent, or Firm*—Barnes & Thornburg

[57] ABSTRACT

The present invention is directed to novel halo-substituted bis-indolemaleimide compounds of the formula:

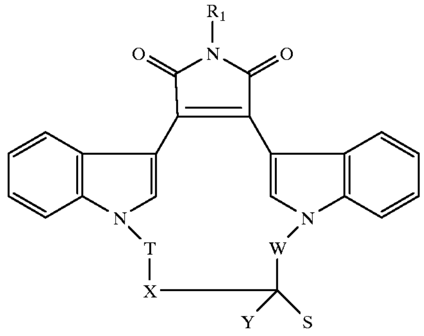

The invention further provides a method of preparing the disclosed compounds and the preparation of pharmaceutical formulation for use in inhibiting Protein Kinase C in mammals.

26 Claims, No Drawings

HALO-SUBSTITUTED BISINDOLEMALEIMIDE PROTEIN KINASE C INHIBITORS

CROSS-REFERENCE TO RELATED APPLICATIONS

This application claims the benefit of U.S. Provisional Application No. 60/016,382, filed May 1, 1996.

Protein kinase C (PKC) consists of a family of closely related enzymes that function as serine/threonine kinases. Protein kinase C plays an important role in cell-cell signaling, gene expression, and in the control of cell differentiation and growth. At present, there are currently at least ten known isozymes of PKC that differ in their tissue distribution, enzymatic specificity, and regulation. Nishizuka Y. *Annu. Rev. Biochem.* 58: 31–44 (1989); Nishizuka Y. *Science* 258: 607–614 (1992).

Protein kinase C isozymes are single polypeptide chains ranging from 592 to 737 amino acids in length. The isozymes contain a regulatory domain and a catalytic domain connected by a linker peptide. The regulatory and catalytic domains can be further subdivided into constant and variable regions. The catalytic domain of protein kinase C is very similar to that seen in other protein kinases while the regulatory domain is unique to the PKC isozymes. The PKC isozymes demonstrate between 40–80% homology at the amino acid level among the group. However, the homology of a single isozyme between different species is generally greater than 97%.

Protein kinase C is a membrane-associated enzyme that is allosterically regulated by a number of factors, including membrane phospholipids, calcium, and certain membrane lipids such as diacylglycerols that are liberated in response to the activities of phospholipases. Bell, R. M. and Burns, D. J., *J. Biol. Chem.* 266: 4661–4664 (1991); Nishizuka, Y. *Science* 258: 607–614 (1992). The protein kinase C isozymes, alpha, beta-1, beta-2 and gamma, require membrane phospholipid, calcium and diacylglycerol/phorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipid for their activation.

Only one or two of the protein kinase C isozymes may be involved in a given disease state. For example, the elevated blood glucose levels found in diabetes lead to an isozyme-specific elevation of the beta-2 isozyme in vascular tissues. Inoguchi et al., *Proc. Natl. Acad. Sci. USA* 89: 11059–11065 (1992). A diabetes-linked elevation of the beta isozyme in human platelets has been correlated with their altered response to agonists. Bastyr III, E. J. and Lu, J. *Diabetes* 42: (Suppl. 1) 97A (1993). The human vitamin D receptor has been shown to be selectively phosphorylated by protein kinase C beta. This phosphorylation has been linked to alterations in the functioning of the receptor. Hsieh et al., *Proc. Natl. Acad. Sci. USA* 88: 9315–9319 (1991); Hsieh et al., *J. Biol. Chem.* 268: 15118–15126 (1993). In addition, recent work has shown that the beta-2 isozyme is responsible for erythroleukemia cell proliferation while the alpha isozyme is involved in megakaryocyte differentiation in these same cells. Murray et al., *J. Biol. Chem.* 268: 15847–15853 (1993).

The ubiquitous nature of the protein kinase C isozymes and their important roles in physiology provide incentives to produce highly selective PKC inhibitors. Given the evidence demonstrating linkage of certain isozymes to disease states, it is reasonable to assume that inhibitory compounds that are selective to one or two protein kinase C isozymes relative to the other PKC isozymes and other protein kinases are superior therapeutic agents. Such compounds should demonstrate greater efficacy and lower toxicity by virtue of their specificity.

Staurosporine, a microbial indolocarbazole, is a potent inhibitor of protein kinase C that interacts with the catalytic domain of the enzyme. Tamaoki et al., *Biochem. Biophys. Res. Commun.* 135: 397–402 (1986); Gross et al., *Biochem. Pharmacol.* 40: 343–350 (1990). However, the therapeutic usefulness of this molecule and closely related compounds is limited by the lack of specificity for protein kinase C over other protein kinases. Ruegg, U. T. and Burgess, G M., *Trends Pharmacol. Sci.* 10: 218–220 (1989). This lack of selectivity results in unacceptable toxicity in this class of molecules.

An additional class of compounds related to staurosporine, the bisindolemaleimides, has been the focus of recent work. Davis et al., *FEBS Lett.* 259: 61–63 (1989); Twoemy et al., *Biochem. Biophys. Res. Commun.* 171: 1087–1092 (1990); Toullec et al., *J. Biol. Chem.* 266: 15771–15781 (1991); Davis et al., *J. Med. Chem.* 35: 994–1001 (1992); Bitetal., *J. Med. Chem.* 36: 21–29 (1993). Some of these compounds have demonstrated selectivity for protein kinase C over other protein kinases.

Although compounds that demonstrate specificity to protein kinase C have been discovered, very little is known regarding isozyme selectivity. For example, analysis of the isozyme selectivity of staurosporine, shows little isozyme selectivity with the exception of poor inhibition of the zeta isozyme relative to the other isozymes. 50 McGlynn et al., *J. Cell. Biochem.* 49: 239–250 (1992); Ward, N. E., and O'Brian, C. A., *Malec. Pharmacol.* 41: 387–392 (1992). Studies of the PKC-selective compound, 3-[1-(3-dimethylaminopropyl)-indol-3-yl]-4-(1H-indol-3-yl)-1H-pyrrole-2,5-dione, suggest a slight selectivity for the calcium dependent isozymes. Toullec et al., *J. Biol. Chem.* 266: 15771–15781 (1991). Subsequent studies of this compound observed no difference, or possibly slight selectivity, for alpha over beta-1 and beta-2 isozymes. Martiny-Baron et al., *J. Biol. Chem.* 268: 9194–9197 (1993); Wilkinson, et al., *Biochem. J.* 294: 335–337 (1993). Therefore, despite years of research and the identification of classes of compounds that inhibit protein kinase C versus other protein kinases, there remains a need for therapeutically effective isozyme-selective inhibitors. Isozyme-selective inhibitors have utility in treating conditions associated with diabetes mellitus and its complications, in addition to treating ischemia, inflamation, central nervous system disorders, cardiovascular disease, dermatological disease and cancer.

One embodiment of the present invention are PKC inhibitors of Formula I:

I

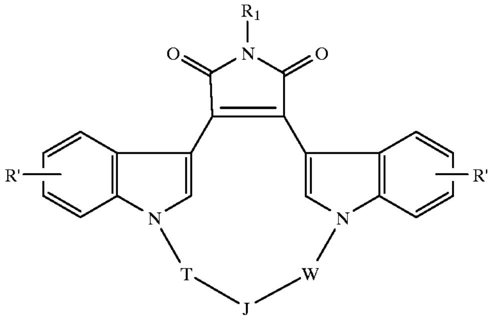

wherein;

R' is independently hydrogen, halo, hydroxy, $C_1$–$C_4$ alkyl, $C_1$–$C_4$ alkoxy, $NR_3R_4$ or —NHCO($C_1$–$C_4$ alkyl);

T is $C_1$–$C_4$ alkylene optionally substituted with halo or $C_1$–$C_4$ alkyl;

W is $C_1$–$C_2$ alkylene optionally substituted with halo or $C_1$–$C_4$ alkyl;

J is

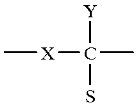

or when T and W are both methylene, J is selected from the group consisting of

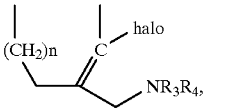

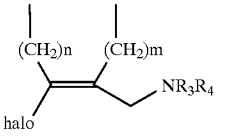 and

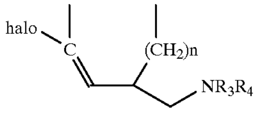

wherein n and m are independently 1 or 2;

X is oxygen, sulfur or a bond between the carbon atoms bridged by X;

Y is halo, $C_1$–$C_4$ alkyl or hydrogen;

$R_1$ is hydrogen or $C_1$–$C_4$ alkyl;

S is —CHO or the group

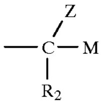

wherein M is hydrogen, —$CH_2OR_5$, —$CH_2NR_3R_4$ or —$NR_3R_4$;

$R_2$ is hydrogen or halo;

Z is hydrogen or —$OR_6$;

wherein $R_3$ and $R_4$ are independently hydrogen, $C_1$–$C_4$ alkyl, halo($C_1$–$C_4$ alkyl), $C_1$–$C_4$ alkanoyl, halo($C_1$–$C_4$ alkanoyl) or taken together with the N atom to which they are bound form a 5 or 6-membered ring; and $R_5$ and $R_6$ are independently hydrogen, $C_1$–$C_4$ alkyl, halo($C_1$–$C_4$ alkyl), $C_1$–$C_4$ alkanoyl, halo($C_1$–$C_4$ alkanoyl) or together form a divalent group selected from the group consisting of —$CR_7R_8$— wherein $R_7$ and $R_8$ are independently hydrogen, $C_1$–$C_4$ alkyl or halo($C_1$–$C_4$ alkyl) or $R_7$ and $R_8$ taken together with the C atom to which they are bound form a 5 or 6-membered ring provided that at least one of Y, S, T or W is halo or a halo substituted group, or T and W are both methylene.

In accordance with another embodiment of the present invention novel intermediates of the Formula II are also provided:

II

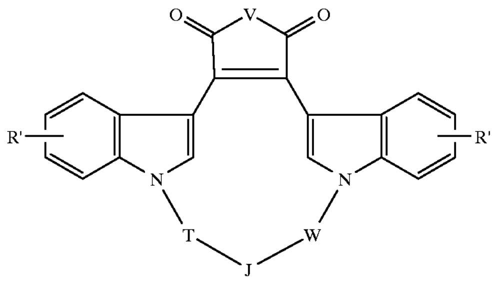

wherein;

R' is independently hydrogen, halo, hydroxy, $C_1$–$C_4$ alkyl, $C_1$–$C_4$ alkoxy, $NR_3R_4$ or —NHCO($C_1$–$C_4$ alkyl);

V is oxygen or

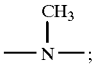;

T is $C_1$–$C_4$ alkylene optionally substituted with halo or $C_1$–$C_4$ alkyl;

W is $C_1$–$C_2$ alkylene optionally substituted with halo or $C_1$–$C_4$ alkyl;

J is

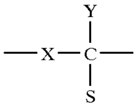

or when T and W are both methylene, J is selected from the group consisting of

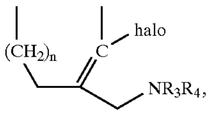

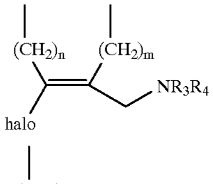 and

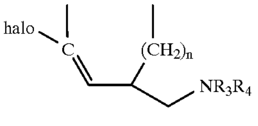

wherein n and m are independently 1 or 2;

X is oxygen, sulfur or a bond between the carbon atom bridged by X;

Y is halo, $C_1$–$C_4$ alkyl or hydrogen;

S is —CHO or the group

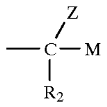

wherein M is hydrogen, $—CH_2OR_5$, $—CH_2NR_3R_4$ or $—NR_3R_4$;

$R_2$ is hydrogen or halo;

Z is hydrogen or $—OR_6$;

wherein $R_3$ and $R_4$ are independently hydrogen, $C_1$–$C_4$ alkyl, halo($C_1$–$C_4$ alkyl), $C_1$–$C_4$ alkanoyl, halo($C_1$–$C_4$ alkanoyl) or taken together with the N atom to which they are bound form a 5 or 6-membered ring; and $R_5$ and $R_6$ are independently hydrogen, $C_1$–$C_4$ alkyl, halo($C_1$–$C_4$ alkyl), $C_1$–$C_4$ alkanoyl, halo($C_1$–$C_4$ alkanoyl) or together form a divalent group selected from the group consisting of $—CR_7R_8—$ wherein $R_7$ and $R_8$ are independently hydrogen, $C_1$–$C_4$ alkyl or halo($C_1$–$C_4$ alkyl) or $R_7$ and $R_8$ taken together with the C atom to which they are bound form a 5 or 6-membered ring provided that at least one of Y, S, T or W is halo or a halo substituted group, or T and W are both methylene.

One aspect of the present invention is a method of preparing the compounds of Formula I comprising the steps of combining at a concentration of about 0.001 molar to about 1.5 molar of a compound of the formula:

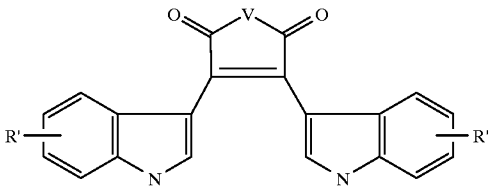

wherein V is oxygen or $NCH_3$;

R' is independently hydrogen, halo, hydroxy, $C_1$–$C_4$ alkyl, $C_1$–$C_4$ alkoxy, $NR_3R_4$ or —NHCO($C_1$–$C_4$ alkyl); and an alkylating agent at a concentration of about 0.001 molar to about 1.5 molar of the formula:

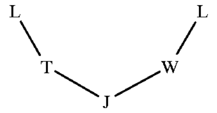

wherein

L is a leaving group;

T is $C_1$–$C_4$ alkylene optionally substituted with halo or $C_1$–$C_4$ alkyl;

W is $C_1$–$C_2$ alkylene optionally substituted with halo or $C_1$–$C_4$ alkyl;

J is

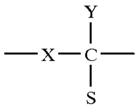

or when T and W are both methylene, J is selected from the group consisting of

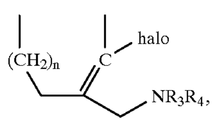,
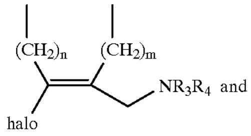 and
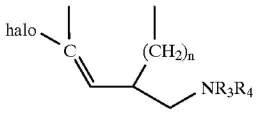

wherein n and m are independently 1 or 2;

X is oxygen, sulfur or a bond between the carbon atom bridged by X;

Y is halo, $C_1$–$C_4$ alkyl or hydrogen;

S is —CHO or the group

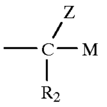

wherein M is hydrogen, $—CH_2OR_5$, $—CH_2NR_3R_4$ or $—NR_3R_4$;

$R_2$ is hydrogen or halo; and

Z is hydrogen or $—OR_6$;

wherein $R_3$ and $R_4$ are independently hydrogen, $C_1$–$C_4$ alkyl, halo($C_1$–$C_4$ alkyl), $C_1$–$C_4$ alkanoyl, halo($C_1$–$C_4$ alkanoyl) or taken together with the N atom to which they are bound form a 5 or 6-membered ring; and $R_5$ and $R_6$ are independently hydrogen, $C_1$–$C_4$ alkyl, halo($C_1$–$C_4$ alkyl), $C_1$–$C_4$ alkanoyl, halo($C_1$–$C_4$ alkanoyl) or together form a divalent group selected from the group consisting of $—CR_7R_8—$ wherein $R_7$ is hydrogen or methyl and $R_8$ is $C_1$–$C_4$ alkyl, halo($C_1$–$C_4$ alkyl) or taken together with the C atom to which they are bound form a 5 or 6-membered ring, and about 0.5 to about 10 equivalents of $Cs_2CO_3$ at a rate of about 0.1 mL/hour to about 2.0 mL/hour in a polar aprotic solvent.

In accordance with one embodiment of the present invention, a compound of Formula III is provided:

III

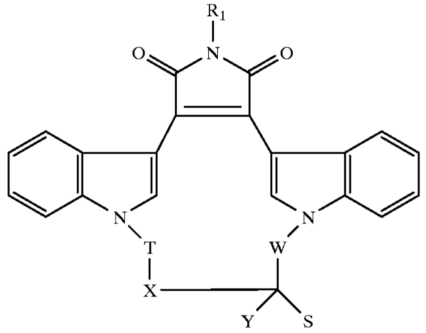

wherein;

$R_1$ is $C_1$–$C_4$ alkyl or hydrogen;

T is $C_2$–$C_4$ alkylene optionally substituted with halo or $C_1$–$C_4$ alkyl;

W is ethylene optionally substituted with halo or $C_1$–$C_4$ alkyl;

X is oxygen, sulfur or a bond between the carbon atom bridged by X;

Y is halo, $C_1$–$C_4$ alkyl or hydrogen;

S is —CHO or the group

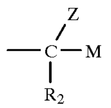

wherein M is hydrogen, —$CH_2OR_5$, —$CH_2NR3R_4$ or —$NR_3R_4$;

$R_2$ is hydrogen or halo; and

Z is hydrogen or —$OR_6$;

wherein $R_3$ and $R_4$ are independently hydrogen, $C_1$–$C_4$ alkyl, halo($C_1$–$C_4$ alkyl), $C_1$–$C_4$ alkanoyl, halo($C_1$–$C_4$ alkanoyl) or taken together with the N atom to which they are bound form a 5 or 6-membered ring; and $R_5$ and $R_6$ are independently hydrogen, $C_1$–$C_4$ alkyl, halo($C_1$–$C_4$ alkyl), $C_1$–$C_4$ alkanoyl, halo($C_1$–$C_4$ alkanoyl) or together form a divalent group selected from the group consisting of —$CR_7R_8$— wherein $R_7$ is hydrogen or methyl and $R_8$ is $C_1$–$C_4$ alkyl, halo($C_1$–$C_4$ alkyl) or taken together with the C atom to which they are bound form a 5 or 6-membered ring provided that at least one of Y, S, T or W is halo or a halo substituted group.

In another embodiment of the present invention a compound of Formula IV is provided:

IV

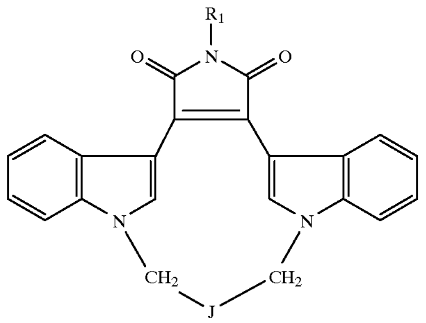

wherein

J is selected from the group consisting of

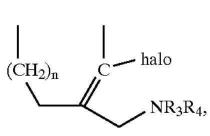
,
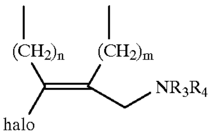
and
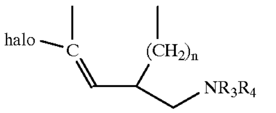

wherein $R_1$ is alkyl or hydrogen;

n and m are independently 1 or 2; and $R_3$ and $R_4$ are independently hydrogen, $C_1$–$C_4$ alkyl, halo($C_1$–$C_4$ alkyl), $C_1$–$C_4$ alkanoyl, halo ($C_1$–$C_4$ alkanoyl) or taken together with the N atom to which they are bound form a 5 or 6-membered ring.

In accordance with one embodiment of the present invention, there is provided a method of inhibiting PKC activity. The method comprises administering to a mammal in need of such treatment, a pharmaceutically effective amount of a compound of Formula I. The present invention is also directed to a method of selectively inhibiting the beta-1 and beta-2 protein kinase C isozymes, the method comprising administering to a mammal in need of such treatment a pharmaceutically effective amount of a compound of the Formula I.

The invention further provides methods for treating conditions that protein kinase C has been demonstrated as having a role in the pathology, such as ischemia, inflammation, central nervous system disorders, cardiovascular disease, dermatological disease, and cancer. The method comprises administering to a mammal in need of treatment a pharmaceutically effective amount of a compound of the Formula I.

This invention is particularly useful in treating diabetic complications. Therefore, the present invention further provides a method for treating diabetes mellitus, which comprises administering to a mammal in need of such treatment a pharmaceutically effective amount of a compound of the Formula I.

One other aspect of this invention is a pharmaceutical formulation comprising a compound of Formula I together with one or more pharmaceutically acceptable excipients, carriers, or diluents.

DETAILED DESCRIPTION OF THE INVENTION

As noted above, the invention provides compounds of Formula I which selectively inhibit protein kinase C. The preferred compounds of this invention are those of Formula I wherein the moieties -T-J-W- contain 4 to 8 atoms, which may be unsubstituted or substituted (with halo or alkyl groups). Most preferably, the moieties -T-J-W- contain 6 atoms. Other preferred compounds of this invention are those compounds of Formula I wherein $R_1$ is hydrogen, and J is

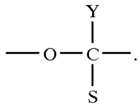
.

One preferred group of compounds are the compounds of the Formula V:

V

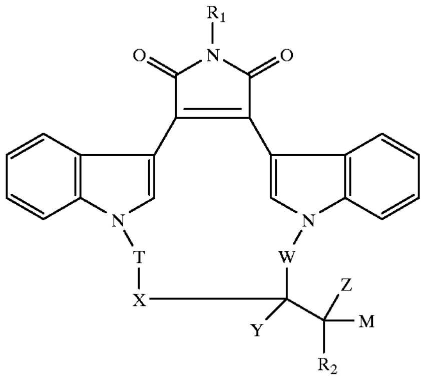

wherein;

$R_1$ is $C_1$–$C_4$ alkyl or hydrogen;

T is $C_2$–$C_4$ alkylene optionally substituted with halo or $C_1$–$C_4$ alkyl;

W is ethylene optionally substituted with halo or $C_1$–$C_4$ alkyl;

X is oxygen, sulfur or a bond between the carbon atom bridged by X;

Y is halo, $C_1$–$C_4$ alkyl or hydrogen;

M is hydrogen, —$CH_2OR_5$, —$CH_2NR_3R_4$ or —$NR_3R_4$;

$R_2$ is hydrogen or halo;

Z is hydrogen or —$OR_6$;

wherein $R_3$ and $R_4$ are independently hydrogen, $C_1$–$C_4$ alkyl, halo($C_1$–$C_4$ alkyl), $C_1$–$C_4$ alkanoyl, halo($C_1$–$C_4$ alkanoyl) or taken together with the N atom to which they are bound form a 5 or 6-membered ring; and $R_5$ and $R_6$ are independently hydrogen, $C_1$–$C_4$ alkyl, halo($C_1$–$C_4$ alkyl), $C_1$–$C_4$ alkanoyl, halo($C_1$–$C_4$ alkanoyl) or together form a divalent group selected from the group consisting of —$CR_7R_8$— wherein $R_7$ is hydrogen or methyl and $R_8$ is $C_1$–$C_4$ alkyl, halo($C_1$–$C_4$ alkyl) or taken together with the C atom to which they are bound form a 5 or 6-membered ring, and wherein at least one of Y, $R_2$, Z, M, T or W is halo or a halo substituted group, more preferably, fluoro or a fluoro substituted group.

Preferred compounds of Formula V include compounds wherein X is oxygen, $R_1$ is hydrogen, T is $C_2$–$C_3$ alkylene, optionally substituted and W is ethylene, optionally substituted. Preferably the T and/or w are substituted with one or more fluoro groups.

In another embodiment of the present invention a compound of Formula VI is provided:

VI

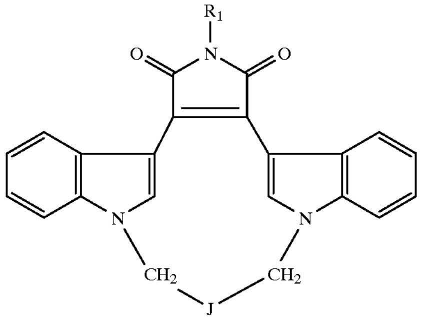

wherein

J is selected from the group consisting of

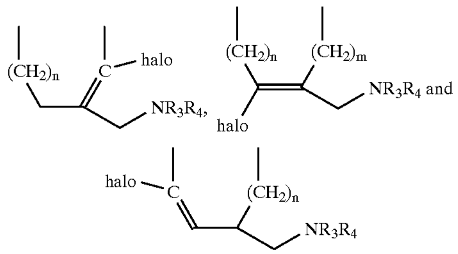

wherein $R_1$ is alkyl or hydrogen;

n and m are independently 1 or 2; and $R_3$ and $R_4$ are independently hydrogen, $C_1$–$C_4$ alkyl, halo($C_1$–$C_4$ alkyl), $C_1$–$C_4$ alkanoyl, halo($C_1$–$C_4$ alkanoyl) or taken together with the N atom to which they are bound form a 5 or 6-membered ring.

The term "halo" represents fluoro, chloro, bromo, or iodo.

The term "$C_1$–$C_4$ alkyl" refers to a cyclo, straight or branched chain alkyl group having from one to four carbon atoms such as methyl, ethyl, n-propyl, isopropyl, cyclopropyl, n-butyl, isobutyl, sec-butyl, t-butyl and the like. Similarly, a "$C_2$–$C_4$ alkyl" represents a cyclo, straight or branched chain alkyl group having two to four carbon atoms. A haloalkyl group is an alkyl group substituted with one or more halo atoms, preferably one to three halo atoms. One example of a haloalkyl group is trifluoromethyl. A $C_1$–$C_4$ alkoxy is a $C_1$–$C_4$ alkyl group covalently bonded through an —0— linkage.

The term "$C_1$–$C_4$ alkylene" is a straight chain alkylene moiety of the formula —$(CH_2)_r$—, wherein r is one to four. Examples of $C_1$–$C_4$ alkylene include methylene, ethylene, trimethylene, tetramethylene and the like. Similarly, a "$C_2$–$C_4$ alkylene" represents a two to four carbon, straight alkylene moiety.

The term "$C_1$–$C_4$ alkenylene" represent a one to four carbon straight chain hydrocarbon containing one or more double bonds, typically one or two double bonds. Examples of C2–C4 alkenylene groups include ethenylene, propenylene, and 1,3-butadieneyl.

The term "$C_1$–$C_4$ alkanoyl" is the acyl residue of a $C_1$–$C_4$ carboxylic acid. Examples of $C_1$–$C_4$ alkanoyl groups are acetyl, propanoyl, butanoyl and the like. A haloalkanoyl group is an alkanoyl group substituted with one or more halo atoms, typically one to three halo atoms. An example of a haloalkanoyl group is trifluoroacetyl.

The term "leaving group" as used in the specification is understood by those skilled in the art. Generally, a leaving group is any group or atom that enhances the electrophilicity of the atom to which it is attached for displacement. Preferred leaving groups are triflate, mesylate, tosylate, imidate, chloride, bromide, and iodide.

The term "carboxy protecting group" (P) as used in the specification refers to one of the ester derivatives of the carboxylic acid group commonly employed to block or protect the carboxylic acid group while reactions are carried out on other functional groups on the compound. The species of carboxy-protecting group employed is not critical so long as the derivatized carboxylic acid is stable to the condition of subsequent reactions and can be removed at the appropriate point without disrupting the remainder of the molecule. T. W. Greene and P. Wuts, *Protective Groups in Organic Synthesis*, John Wiley and Sons, New York, N.Y., 1991, Chapter 5, provide a list of commonly employed protecting groups. See also E. Haslam, *Protective Groups in Organic Chemistry*, J. G. W. McOmie, Ed., Plenum Press, New York, N.Y., 1973. A related term is "protected carboxy," which refers to a carboxy group protected with a carboxy protecting group.

The term "hydroxy protecting group" (P) as used in the specification refers to one of the ether or ester derivatives of the hydroxy group commonly employed to block or protect the hydroxy group while reactions are carried out on other functional groups on the compound. The species of hydroxy protecting group employed is not critical so long as the derivatized hydroxy group is stable to the condition of subsequent reactions and can be removed at the appropriate point without disrupting the remainder of the molecule. T. W. Greene and P. Wuts, *Protective Groups in Organic Synthesis*, John Wiley and Sons, New York, N.Y., 1991, provide a list of commonly employed protecting groups. Preferred hydroxy protecting groups are tertbutyldiphenylsilyloxy (TBDPS), tert-butyldimethylsilyloxy (TBDMS), triphenylmethyl (trityl), methoxytrityl, or an alkyl or aryl ester. A related term is "protected hydroxy," which refers to a hydroxy group protected with a hydroxy protecting group.

The term "amino protecting group" (P) as used in the specification refers to substituents of the amino group commonly employed to block or protect the amino functionality while reacting other functional groups on the compound. The species of amino-protecting group employed is not critical so long as the derivatized amino group is stable to the condition of subsequent reactions and can be removed at the appropriate point without disrupting the remainder of the molecule. T. W. Greene and P. Wuts, *Protective Groups in Organic Synthesis*, Chapter 7, provide a list of commonly employed protecting groups. See also J. W. Barton, *Protective Groups in Organic Chemistry*, Chapter 2. Preferred amino-protecting groups are t-butoxycarbonyl, pthalide, a cyclic alkyl, and benzyloxycarbonyl. The related term "protected amino" defines an amino group substituted with an amino protecting group as defined.

The term "—NH protective groups" as used in the specification refers to sub-class of amino protecting groups that are commonly employed to block or protect the —NH functionality while reacting other functional groups on the compound. The species of protecting group employed is not critical so long as the derivatized amino group is stable to the condition of subsequent reactions and can be removed at the appropriate point without disrupting the remainder of the molecule. T. W. Greene and P. Wuts, *Protective Groups in Organic Synthesis*, Chapter 7, page 362–385, provide a list of commonly employed protecting groups. Preferred —NH protecting groups are carbamate, amide, alkyl or aryl sulfonamide. The related term "protected —NH" defines a group substituted with an —NH protecting group as defined.

The term "pharmaceutically effective amount", as used herein, represents an amount of a compound of the invention that is capable of inhibiting PKC activity in mammals. The particular dose of the compound administered according to this invention will, of course, be determined by the particular circumstances surrounding the case, including the compound administered, the route of administration, the particular condition being treated, and similar considerations. The compounds can be administered by a variety of routes including the oral, rectal, transdermal, subcutaneous, topical, intravenous, intramuscular or intranasal routes. For all indications, a typical daily dose will contain from about 0.01 mg/kg to about 20 mg/kg of the active compound of this invention. Preferred daily doses will be about 0.05 to about 10 mg/kg, ideally about 0.1 to about 5 mg/kg. However, for topical administration a typical dosage is about 1 to about 500 $\mu$g compound per $cm^2$ of an affected tissue. Preferably, the applied amount of compound will range from about 30 to about 300 $\mu g/cm^2$, more preferably, from about 50 to about 200 $\mu g/cm^2$, and, most preferably, from about 60 to about 100 $\mu g/cm^2$.

The term "treating," as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder.

The term "isozyme selective" means the preferential inhibition of one protein kinase C isozyme (or subgroup) over the other isozymes. For example a compound may selectively inhibit the beta-1 or beta-2 isozymes over protein kinase C isozymes alpha, gamma, delta, epsilon, zeta, and eta. In general, isozyme selective compounds demonstrate a minimum of a eightfold differential (preferably a ten fold differential) in the dosage required to inhibit one subtype compared to the dosage required for equal inhibition of a different subtype (for example, inhibition of PKC beta-1 or beta-2 isozyme as compared to the alpha protein kinase C isozyme) as measured in the PKC assay. The compounds demonstrate this differential across the range of inhibition and are exemplified at the $IC_{50}$, i.e., a 50% inhibition. Thus, for example, a beta-i and beta-2 isozyme-selective compound inhibits the beta-1 and beta-2 isozymes of protein kinase C at much lower concentrations with lower toxicity by virtue of their minimal inhibition of the other PKC isozymes.

The compounds of Formula I having a basic moiety, eg $NR_3R_4$, can also be in the form of their pharmaceutically acceptable acid addition salts thereof. Acids commonly employed to form such salts include inorganic acids such as hydrochloric, hydrobromic, hydroiodic, sulfuric and phosphoric acid, as well as organic acids such as paratoluenesulfonic, methanesulfonic, oxalic, parabromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycollate, maleate, tartrate, methanesulfonate, propanesulfonate, naphthalene-1-sulfonate, naphthalene-2-sulfonate, mandelate and like salts.

In addition to pharmaceutically-acceptable salts, other salts can be used in accordance with the present invention. They may serve as intermediates in the purification of the compounds, in the preparation of other salts, or in the identification and characterization of the compounds or intermediates.

The pharmaceutically acceptable salts of compounds of Formula I can also exist as various solvates, such as with water, methanol, ethanol, dimethylformamide, ethyl acetate and the like. Mixtures of such solvates can also be prepared. The source of such solvates can be from the solvent of crystallization, inherent in the solvent of preparation or crystallization, or adventitious to such solvent. Such solvates are within the scope of the present invention.

Various stereoisomeric forms of the compounds of Formula I may exist; for example, T or W may include a chiral carbon atom in the substituted alkylene moiety. The compounds of Formula I are typically prepared as racemates and can conveniently be used as such, but individual enantiomers can be isolated or synthesized by conventional techniques if so desired. Such racemates and individual enantiomers and mixtures thereof form part of the present invention.

The present invention also encompasses the pharmaceutically acceptable prodrugs of the compounds of Formula I. A prodrug is a drug which has been chemically modified and may be biologically inactive (at the enzyme's site of action), but can be degraded or modified by one or more enzymatic or other in vivo processes to produce the parent bioactive form. The prodrug preferably has a different pharmacokinetic profile than the parent, enabling easier absorption across the mucosal epithelium, better salt formation or solubility, and/or improved systemic stability (an increase in plasma half-life, for example). Conventional procedures for the selection and preparation of suitable prodrug derivatives are described, (or example, in H, Bundgaard, *Design of Prodrugs*, (1985). Typically, such chemical modifications include the following:

1) ester or amide derivatives which may be cleaved by esterases or lipases;

2) peptides which may be recognized by specific or nonspecific proteases; or 3) derivatives that accumulate at a site of action through membrane selection of a prodrug form; or a modified prodrug form, or any combination of 1 to 3, supra.

The synthesis of certain bis-indole-N-maleimide derivatives is described in Davis et al., U.S. Pat. No. 5,057,614, the disclosure of which is incorporated herein by reference. Generally, the compounds of the present invention may be prepared as follows:

Scheme 1

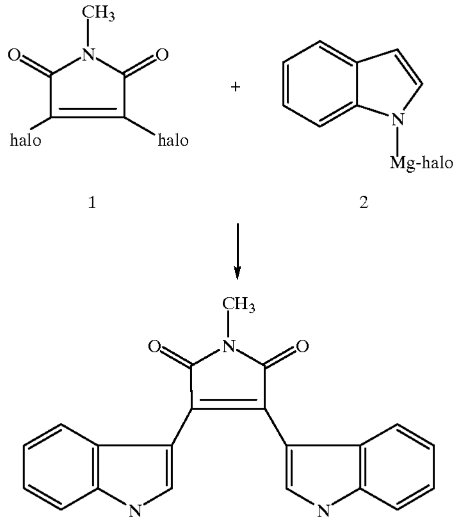

1 2

3

The halo group in accordance with scheme 1 is preferably fluoro, chloro, bromo, or iodo. Compound 1 is preferably 2,3-dichloro N-methylmaleimide. The reaction between Compound 1 and the indole, Compound 2, is commonly known as a Grignard reaction. The reaction is carried out in an inert organic solvent, such as toluene, at a temperature between room temperature and the reflux temperature of the reaction mixture. Most significantly, the reaction depicted in Scheme I is dependent on solvent conditions. When carried out in a toluene:THF:ether solvent system, the reaction provides Compound 3 in greater than 80 percent yield and greater than 95 percent purity. The product is precipitated from the reaction mixture with ammonium chloride, $NH_4Cl$. The resulting intermediate, Compound 3, may be isolated by standard techniques.

Bis-3,4(3'-indolyl)-lN-methyl-pyrrole-2,5-dione, Compound 3, may then be converted by alkaline hydrolysis to the corresponding anhydride of the Formula 4 by techniques known in the art and described in Brenner et al., *Tetrahedron* 44: 2887–2892 (1988). Preferably, Compound 3 is reacted with 5N KOH in ethanol at a temperature ranging from 25° C. to reflux to produce the compound of Formula 4:

4

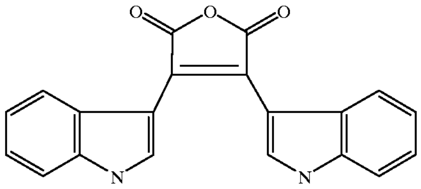

Compounds of Formula 3 are generally more stable than the compounds of the Formula 4. Therefore, it is preferred that Compounds 3 are reacted in accordance with Scheme 2 to produce the compounds of Formula I. However, one skilled in the art would recognize that the compounds of the Formula 4, may also be reacted according to Scheme 2.

Scheme 2

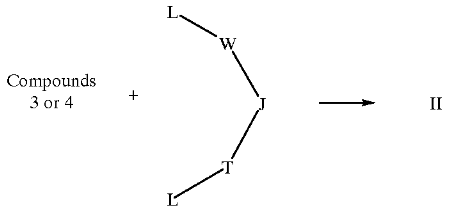

5

T, J, and W are the same as previously defined. L is a good leaving group such as chloro, bromo, iodo, mesyl, tosyl, and the like. L may also be a hydroxy or other precursor that may be readily converted to a good leaving group by techniques known in the art. For example, the hydroxy may be readily converted to a sulfonic ester such as mesyl by reacting the hydroxy with methanesulfonyl chloride to produce the mesylate leaving group.

The reaction represented by Scheme 2 is accomplished by any of the known methods of preparing N-substituted indoles. This reaction usually involves approximately equimolar amounts of the two reagents, although other ratios, especially those wherein the alkylating reagent is in excess, are operative. The reaction is best carried out in a polar aprotic solvent employing an alkali metal salt or other such alkylation conditions as are appreciated in the art. When the leaving group is bromo or chloro, a catalytic amount of iodide salt, such as potassium iodide may be added to speed the reaction. Reaction conditions include the following: Potassium hexamethyldisilazide in dimethylformamide or tetrahydrofuran, sodium hydride in dimethylformamide.

Preferably, the reaction is carried out under slow reverse addition with cesium carbonate in either acetonitrile, dimethylformamide (DMF), or tetrahydrofuran (THF). The temperature of the reaction is preferably from about ambient temperature to about the reflux temperature of the reaction mixture.

One skilled in the art would recognize that the reaction described in Scheme 2 may be employed with the compounds L–T' and L–W' wherein T' and W' are a protected carboxy, protected hydroxy, or a protected amine. After the alkylation of Scheme 2, T' and W' may be converted to moieties capable of coupling to form J. The coupling of T' and W' to form the various ether or thioether derivatives is known in the art and described in, for example Ito et al., *Chem. Pharm. Bull.* 41(6): 1066–1073 (1993); Kato, et al., *J. Chem. Pharm. Bull.* 34: 486 (1986); Goodrow, et al. *Synthesis* 1981: 457; Harpp, et al., *J. Am. Chem. Soc.* 93: 2437 (1971); and Evans, et al., *J. Org. Chem.* 50: 1830 (1985).

One skilled in the art would also recognize that compound 3 may be converted to the compounds of Formula I in a two step synthesis as described in Scheme 3.

Scheme 3

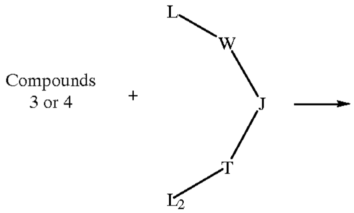

6

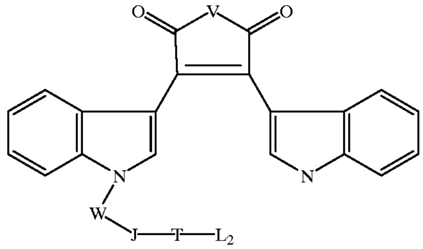

7

II

T, J, W, V and L are as previously defined. L2 is a protected hydroxy or other group that may be readily converted to a good leaving group by techniques known in the art. The coupling between Compound 3 or 4 and Compound 6 is an alkylation as previously discussed. The monoalkylated intermediate, 7, is deprotected, and L2 is converted to a leaving group. For example, if the hydroxy is protected with t-butyldimethylsilyl (TBDMS), TBDMS is selectively removed using acidic methanol. The resulting free hydroxy is then converted to a leaving group, such as an alkyl halide, preferably an alkyl iodide or bromide ($CBr_4$ in triphenylphosphine) or sulfonate (mesyl chloride in triethylamine). The macrolide is then formed by alkylating under slow reverse addition to a solution of base, such as potassium hexamethyldisilazide, or sodium hydride but preferably $Cs_2CO_3$ in a polar aprotic solvent such as acetonitrile, DMF, THF at temperatures ranging from ambient to reflux.

The compounds of Formula I may be prepared in substantially higher yield when the alkylation is carried out under slow reverse addition to $Cs_2CO_3$ in a polar aprotic solvent. Slow reverse addition involves combining a mixture of compound and alkylating agent (Scheme 2) or the compound (Scheme 3) with the base at a rate from about 0.1 mL/hour to about 2.0 mL/hour. The concentration of each reagent in the mixture is about 1.5 molar to about 0.001 molar. When carried out with the monoalkylated compound (Scheme 3) the concentration is from about 3 molar to about 0.001 molar. The slow addition results in a concentration of reagents in the reaction vessel of about 0.01 molar to 1.5 molar. One skilled in the art would recognize that at a higher rate of addition a lower concentration of reagents could be used in the reaction. Likewise, at a slower rate of addition, a higher concentration of reagents could be used in the reaction. Preferably, the compound is added at about 0.14 mL/hour with the compound and the alkylating agent at 0.37 molar. It is preferred that the $Cs_2CO_3$ be added in excess—most preferably a 4:1 ratio $Cs_2CO_3$ to alkylating agent. Preferred polar aprotic solvents are acetonitrile, dimethylformamide (DMF), acetone, dimethylsulfoxide (DMSO), dioxane, diethylene glycol methyl ether (diglyme), tetrahydrofuran (THF), or other polar aprotic solvents in which the reagents are soluble. The reaction is carried out at temperatures ranging from about 0° C. to reflux. One skilled in the art would recognize that the ratio of the mixture of the compound and alkylating agent is not critical. However, it is preferred that the reagents are mixed in a ratio of 0.5 to 3 equivalents of each other. Most preferably, the reagents are mixed 1:1.

When V is N—$CH_3$, Compound II is converted to the corresponding anhydride (V is 0) by alkaline hydrolysis. Alkaline hydrolysis involves reacting the compound with a base (such as sodium hydroxide or potassium hydroxide), in either $C_1$–$C_4$ alcohol (preferably ethanol), DMSO/water, dioxane/water, or acetonitrile/water at a temperature ranging from about 25° C. to preferably about reflux. The concentration of the reactants is not critical.

The anhydride (V is 0) is converted to the maleimide of Formula I by ammonolysis. Ammonolysis involves reacting the anhydride with an excess of hexamethyldisilazane or an ammonium salt (ammonium acetate, bromide, or chloride) and $C_1$–$C_4$ alcohol (preferably methanol) in an polar aprotic solvent such as DMF at room temperature. Preferably, the hexamethyldisilazane or an ammonium salt is reacted at a ratio greater than about 5:1 equivalents of anhydride.

Scheme 4 depicts the preparation of an intermediate useful in accordance with the present invention for preparing the compounds of Formula III, wherein X is O.

Scheme 4

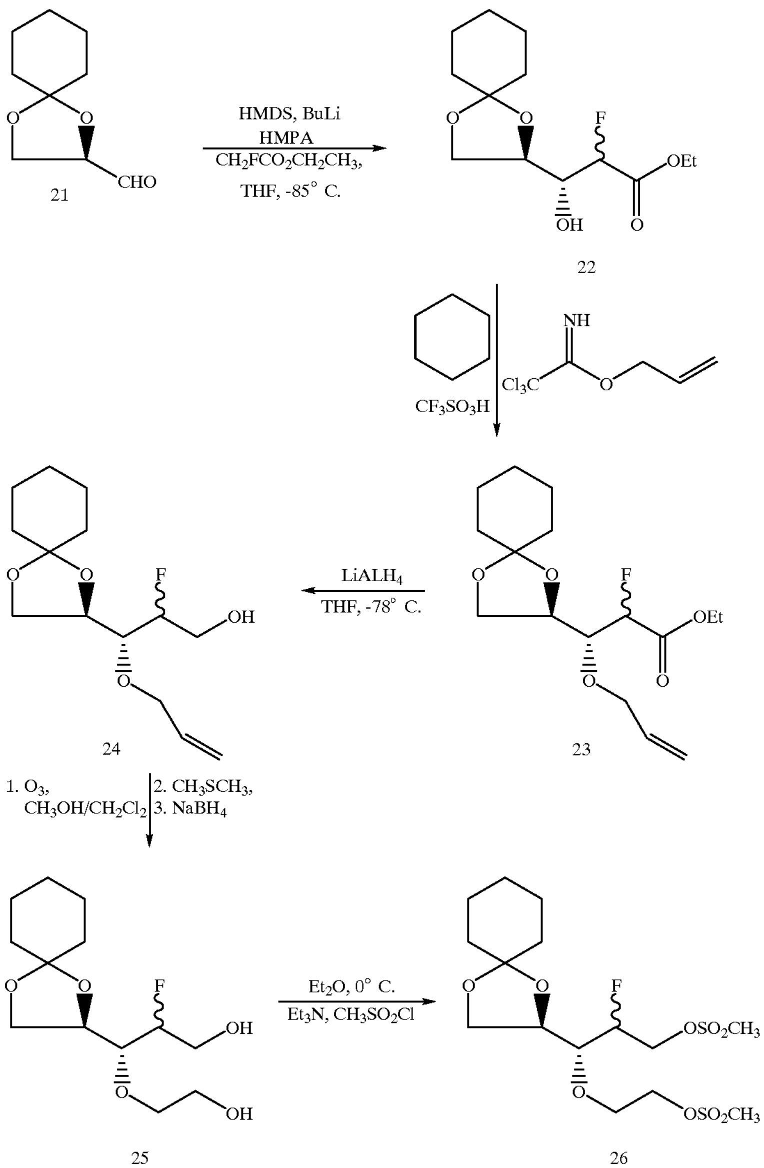

21 22 23 24 25 26

-continued
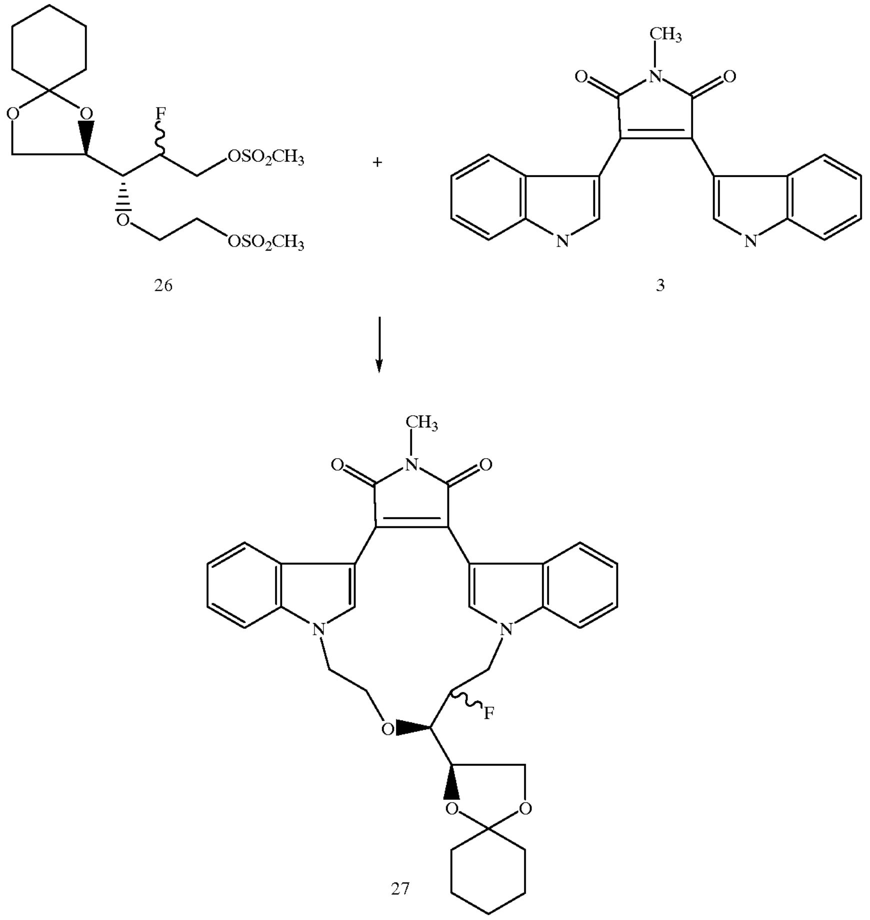
26 3 27
The following examples and preparations are provided merely to further illustrate the invention and not to limit it.
EXAMPLE 1
Synthesis of Bisfluorinated Six Atom Bridged Bisindolylmaleimides
A compound of formula VII:
VII
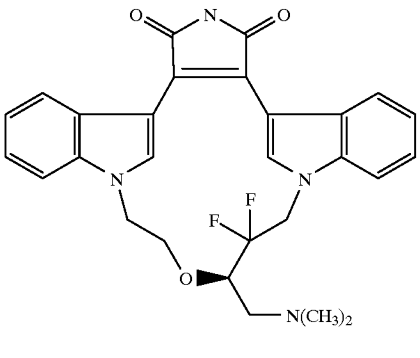
is produced as follows:
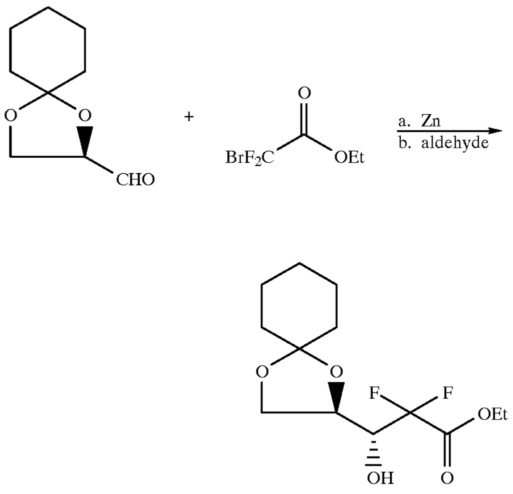
Compound 8a is converted into the compound of Formula VII using the steps outlined in scheme 4.

A compound of formula VIII:

VIII

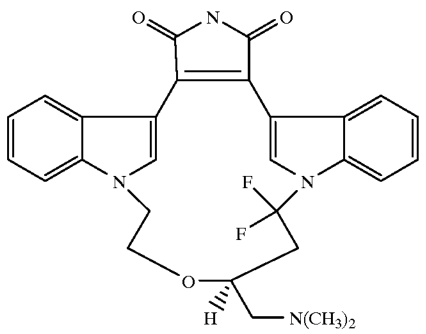

is produced as follows:

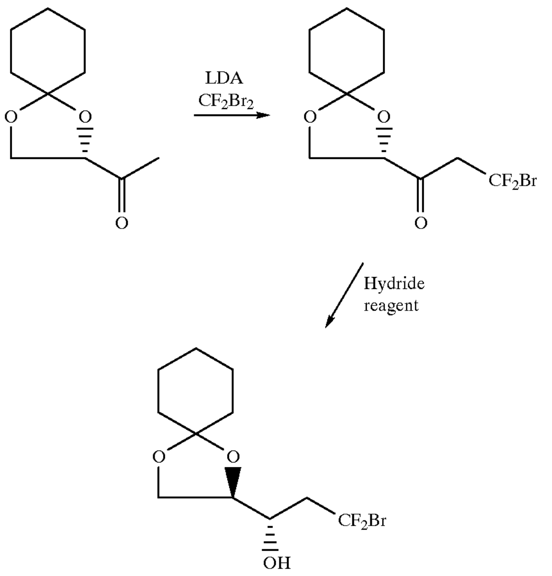

This compound is converted into the compound of Formula VIII using the steps outlined in scheme 4.

A compound of formula IX:

IX

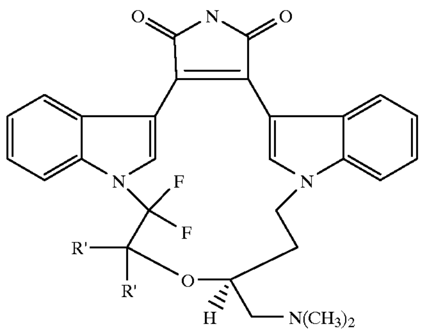

is produced as follows:

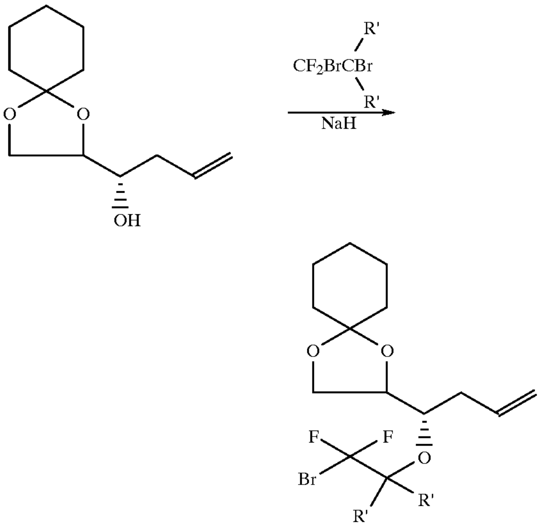

This compound, wherein R' is H or F, is converted into the compound of Formula IX using the steps outlined in scheme 4.

EXAMPLE 2

Synthesis of C2-Monofluorinated Seven Atom Bridged Bisindolylmaleimides

A compound of formula X:

X

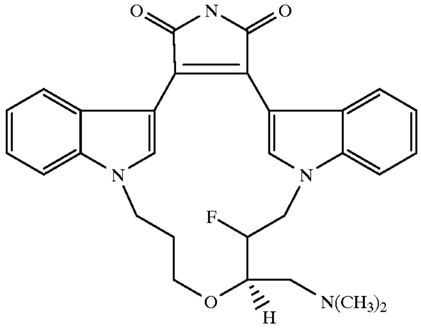

is produced as follows:

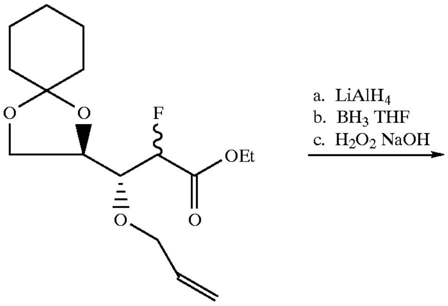

-continued

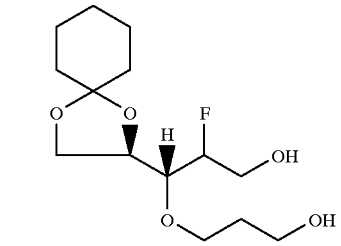

This compound is converted into the compound of Formula X using the steps outlined in scheme 4.

EXAMPLE 3

Synthesis of C6-Monofluorinated Seven Atom Bridged Bisindolylmaleimides

A compound of formula XI:

XI

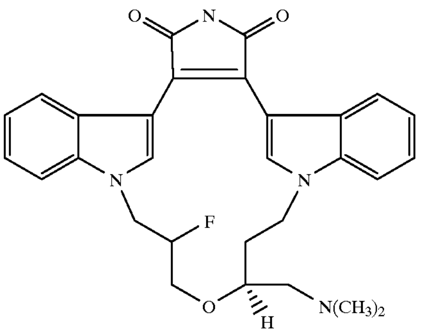

is produced as follows:

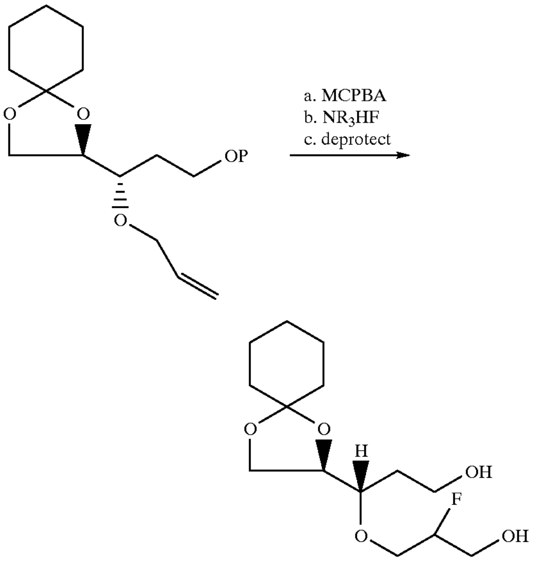

This compound is converted into the compound of Formula XI using the steps outlined in scheme 4.

EXAMPLE 4

Synthesis of C6-Difluorinated Seven Atom Bridged Bisindolylmaleimides

A compound of formula XII:

XII

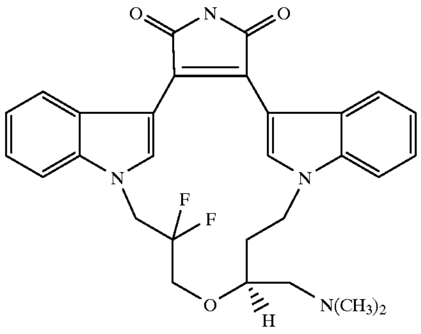

is produced as follows:

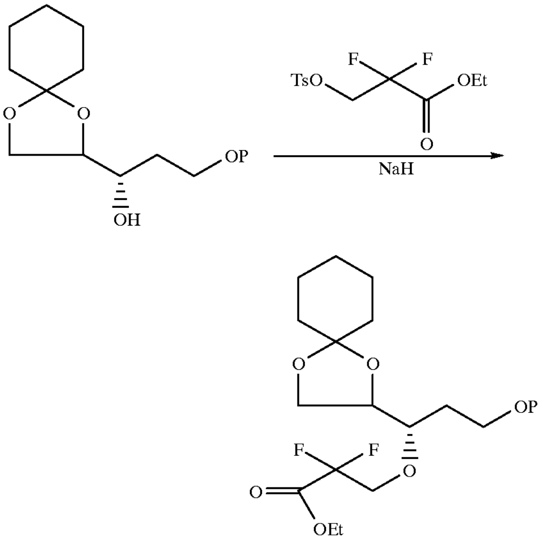

This compound is converted into the compound of Formula XII using the steps outlined in scheme 4.

EXAMPLE 5

Synthesis of Fluorinated Six Atom Thio-Bridged Bisindolylmaleimides

A compound of formula XIII:

XIII

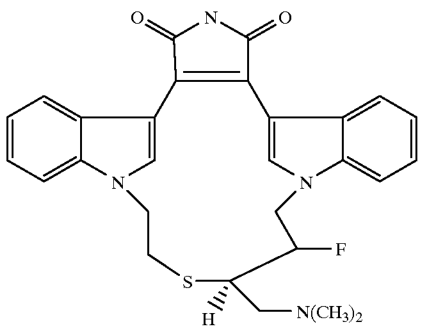

is produced as follows:

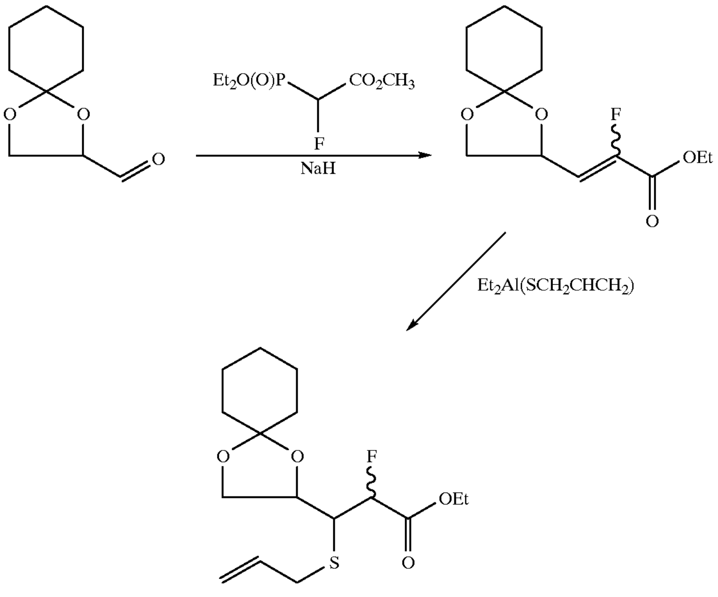

This compound is converted into the compound of Formula XIII using the steps outlined in scheme 4.

EXAMPLE 6

Synthesis of C4-Sidechain derivatives of Fluorinated Six Atom Bridged Bisindolylmaleimides A compound of formula XIV:

XIV

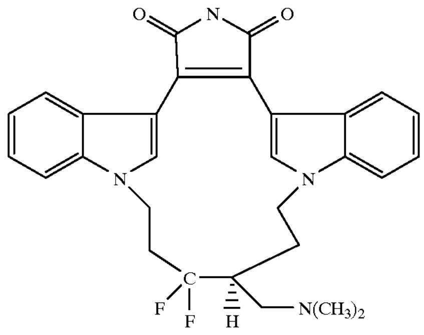

is produced as follows:

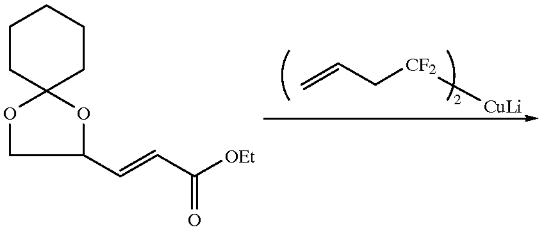

-continued

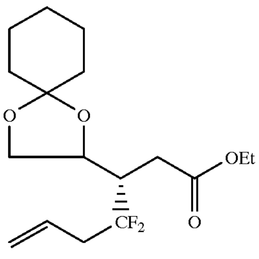

This compound is converted into the compound of Formula XIV using the steps outlined in scheme 4.

EXAMPLE 7

Synthesis of Fluoroalkene Six Atom Bridged Bisindolylmaleimides

A compound of formula XV:

XV

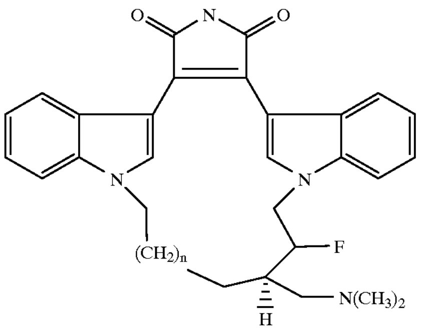

is produced as follows:

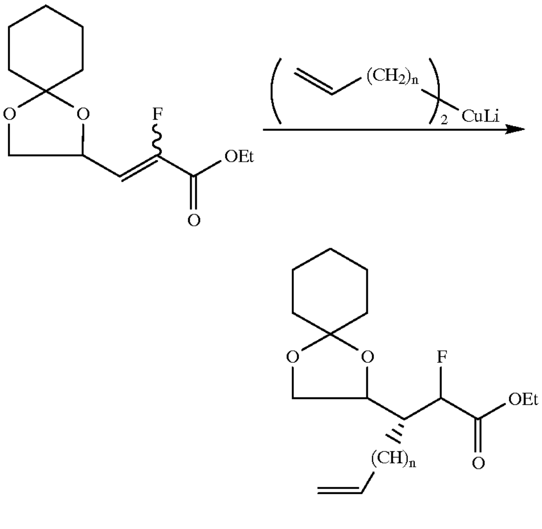

This compound is converted into the compound of Formula XV using the steps outlined in scheme 4.

EXAMPLE 8

Synthesis of Fluoroalkene Seven Atom Bridged Bisindolylmaleimides

A compound of formula XVI:

XVI (E and Z forms)

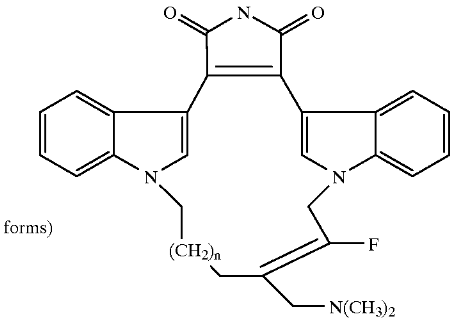

is produced as follows:

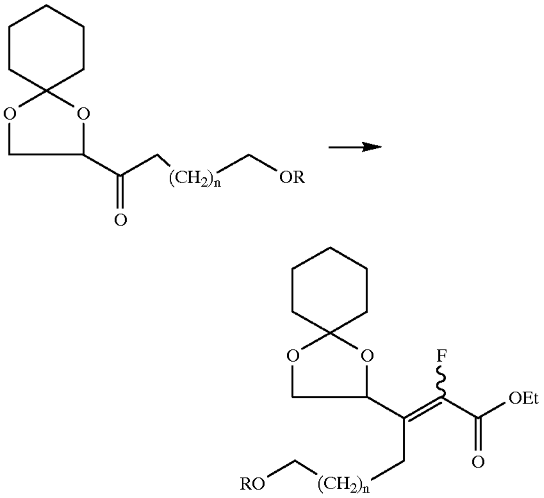

This compound is converted into the compound of Formula XVI using the steps outlined in scheme 4.

A compound of formula XVII:

XVII (E and Z forms)

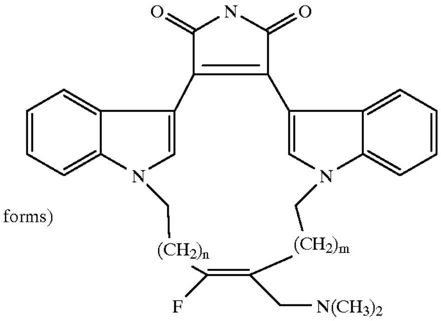

is produced as follows:

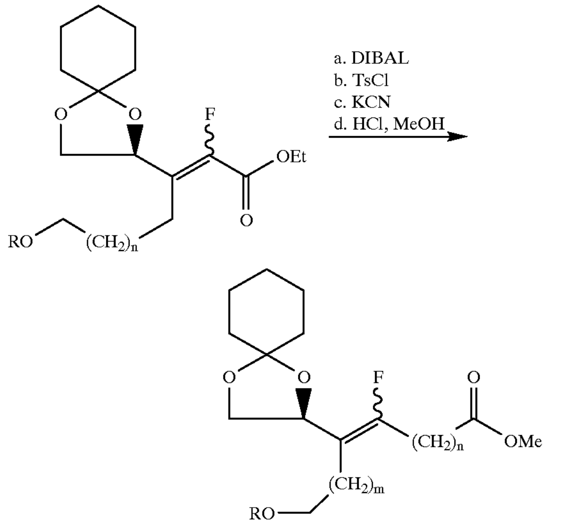

This compound is converted into the compound of Formula XVII using the steps outlined in scheme 4.

A compound of formula XVIII:

XVIII (E and Z forms)

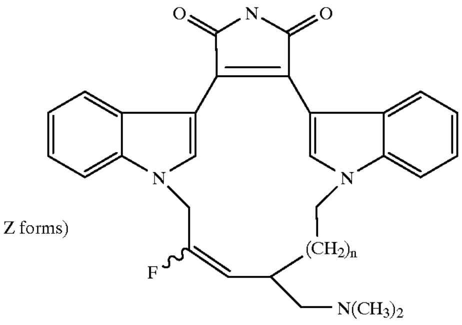

is produced as follows:

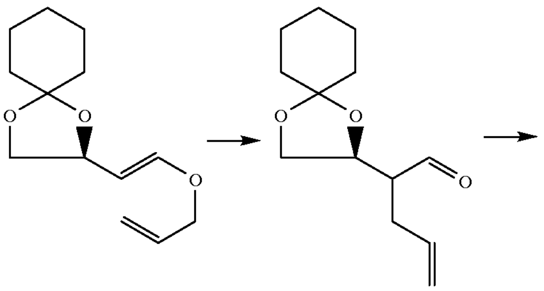

-continued

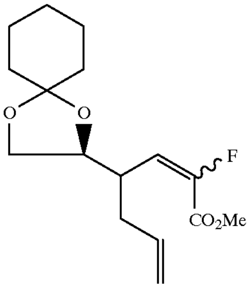

This compound is converted into the compound of Formula XVIII using the steps outlined in scheme 4.

EXAMPLE 9

Synthesis of C2-methylated Fluorinated Six Atom Bridged Bisindolylmaleimides

A compound of formula XIX:

XIX

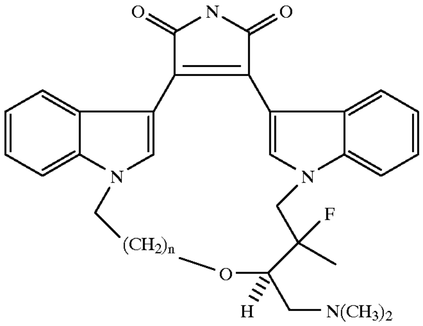

is produced as follows:

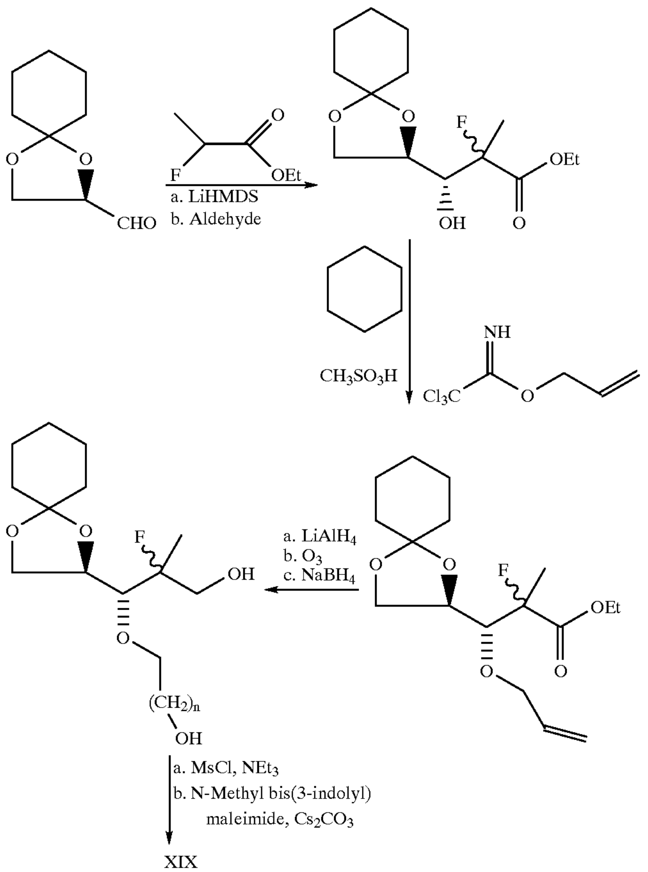
XIX
EXAMPLE 10
Synthesis of C3-Derivative Fluorinated Six Atom Bridged Bisindolylmaleimides

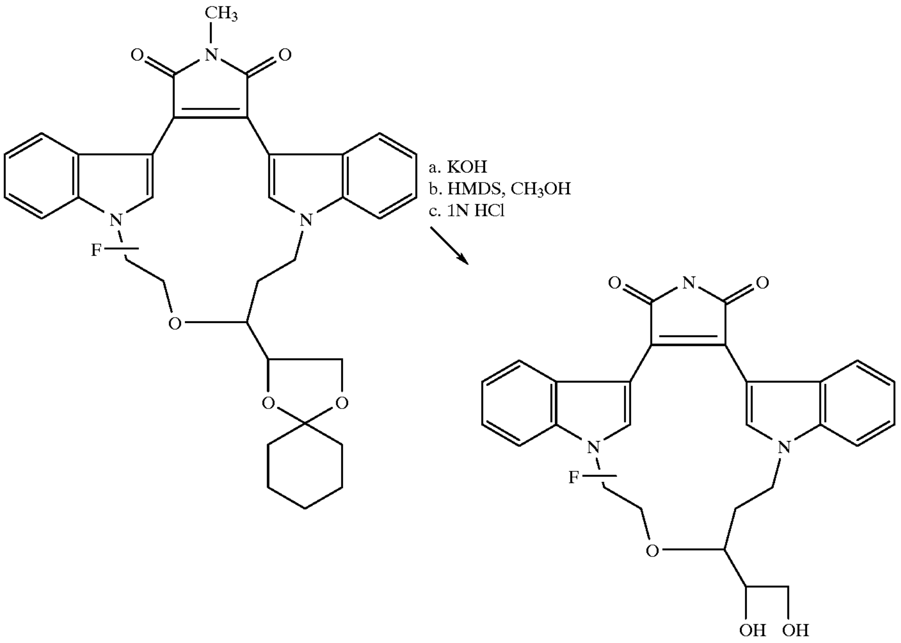
EXAMPLE 11
Synthesis of C3-Derivative Fluorinated Six Atom Bridged Bisindolylmaleimides

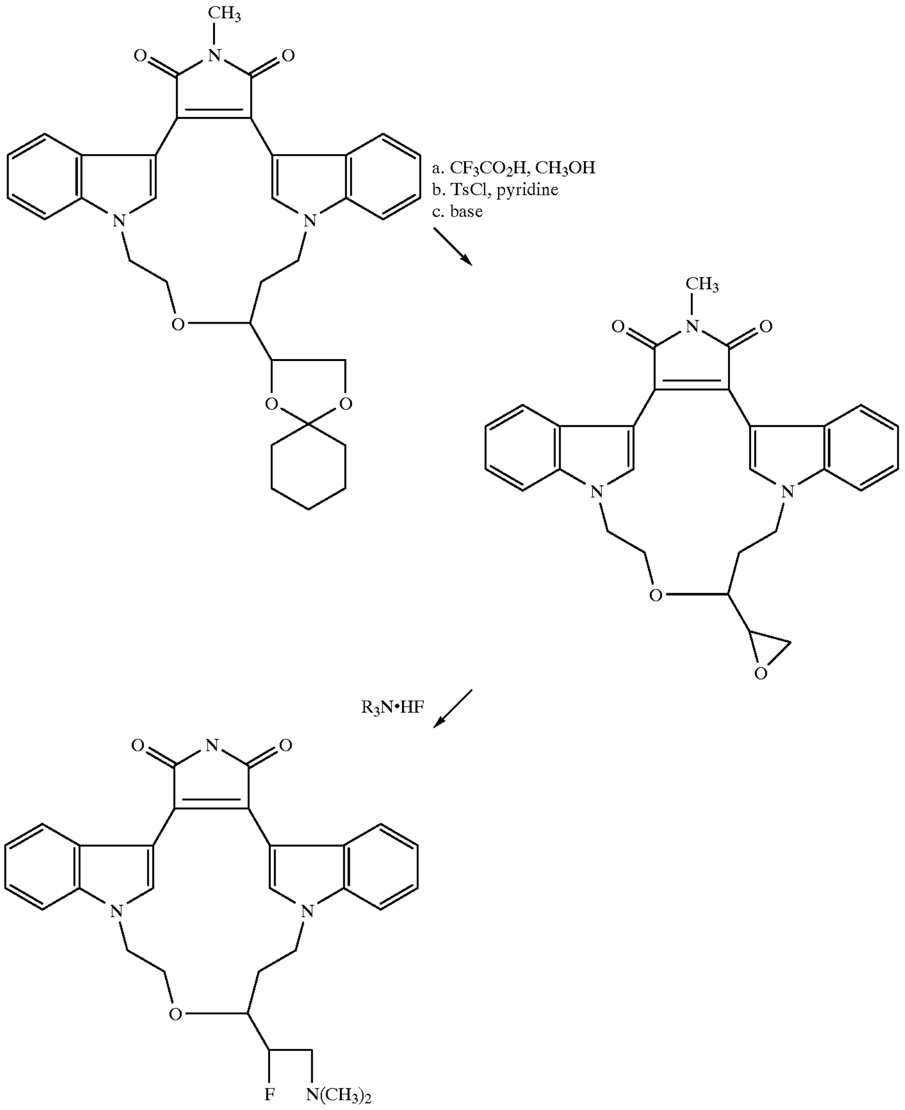
EXAMPLE 12
Synthesis of C3-Derivative Fluorinated Six Atom Bridged Bisindolylmaleimides

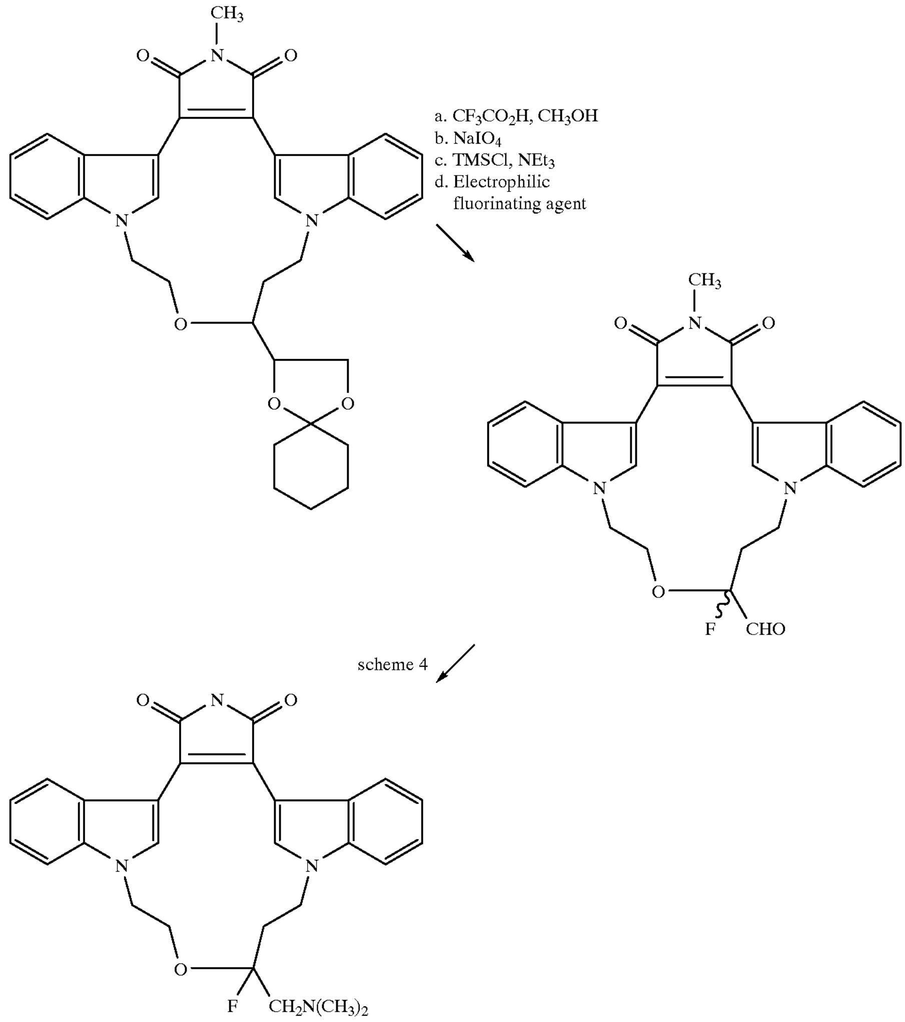

In the following examples and preparations, melting point, nuclear magnetic resonance spectra, mass spectra, high pressure liquid chromatography over silica gel, N,N-dimethylformamide, palladium on charcoal, tetrahydrofuran, and ethyl acetate are abbreviated M.Pt., NMR, MS, HPLC, DMF, Pd/C, THF, and EtOAc , respectively. The terms “NMR” and “MS” indicate that the spectrum was consistent with the desired structure.

EXAMPLE 13

Preparation of the bisindolylmaleimide of the formula

14

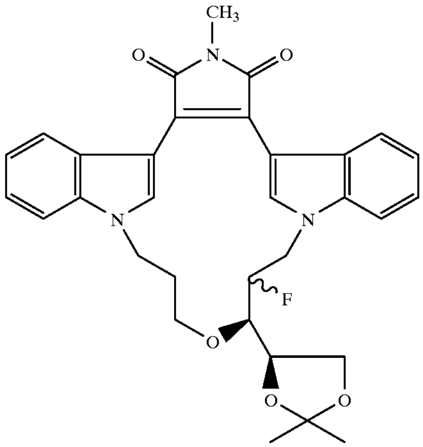

Ethyl (3S,4R)-2-fluoro-3-hydroxy-4,5-O-isopropylidene pentanoate

To a stirred round-bottom flask containing 50 mL of anhydrous THF and 6.1 mL (0.03 mol) of hexamethyl disilazane (HMDS) at 0° C., was added 12 mL (0.03 mol) of a 2.5M solution of butylithium in hexane. The resulting mixture was allowed to return to room temperature and stirred for 10 min. Then it was lowered to −85° C. A mixture of 1.80 g (0.010 mol) of hexamethyl phosphoric triamide (HMPA) and 1.00 mL (0.010 mol) of ethyl fluoroacetate was added dropwise as rapidly as possible while not allowing the temperature to rise above −85° C. After 5 additional min. 880 mg (0.00677 mol) of 2,3–O-isopropylidene D-glyceraldehyde (8) was added. The mixture was stirred for 10 min and then quenched at −85° C. with 5 mL saturated ammonium chloride. On warming to room temperature the mixture was diluted with 80 mL $CH_2Cl_2$ and washed with water (60 mlx3). The $CH_2Cl_2$ layer was separated and dried over $Na_2SO_4$. After evaporation of the volatiles in vacuo, the residue was loaded on a short silica gel column. It was flushed with $CH_2Cl_2$ then 30% $CH_3CN/CCl_4$ (or ethyl acetate), yielding crude product.

The crude product was chromatographed on a silica gel column using 15% (v/v) $CH_3CN/CCl_4$ as eluent, yielding two fractions with partial separation of two diastereomers: fraction 1, 177 mg, (9a, 34%, 9b, 66% based on $^1$HNMR) fraction 2, 377 mg (9a, 62%, 9b, 38%). Overall yield 34.7%, in which 9a, was 52.7%, and 9b, was 47.3%

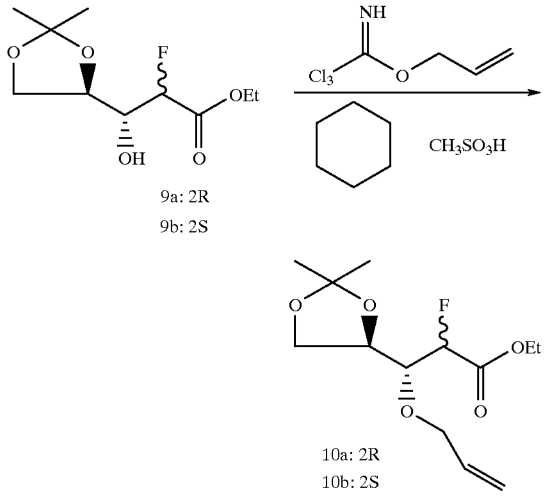

9a: 2R
9b: 2S

10a: 2R
10b: 2S

Ethyl (3S.4R) 3-allyloxy-2-fluoro-4.5-O-isopropylidene pentanoate

Alcohol 9, 327 mg (1.39 mmol, which is a mixture of 9a, 62% and 9b, 38%), was evaporated with toluene and 327 mg (1.39 mmol), was dissolved in 6 mL cyclohexane. Under $N_2$ atmosphere and stirring, allyl trichloroacetimidate (423 μL, 561 mg, 2.78 mmol) was added, followed by trifluoromethanesulfonic acid (20 μL) in 5 μL portions over 20 min. A dark brown oily ppt. began to form instantly. The reaction mixture was stirred at room temperature for 60 h. A white ppt. was formed, and that ppt. was filtered and washed with cyclohexane twice. The filtrate was evaporated to a oily liquid. It was chromatographed on a silica gel column using 10% (v/v) ethyl acetate-hexane as eluent, affording two fractions. The first fraction contained mainly 10a and the second fraction 10b. The fractions were purified on a silica column using 25% (v/v) hexane/$CH_2Cl_2$ as eluent, yielding 10a, 133 mg (34.8%) and 10b, 83 mg (21.7%). Total yield 56.5%.

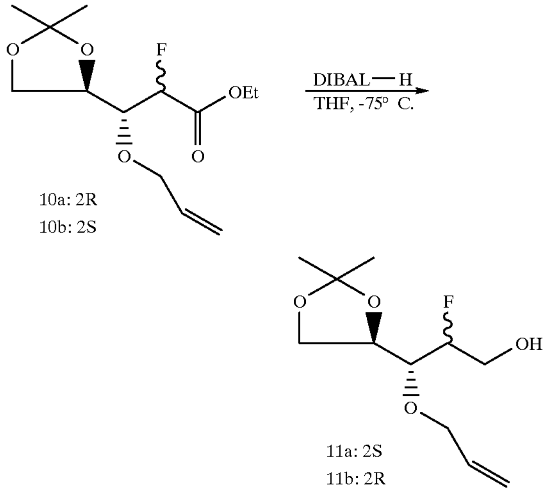

10a: 2R
10b: 2S

11a: 2S
11b: 2R (3S,4R) 3-Allyloxy-2-fluoro-4,5-O-isopropylidene pentanol (11)

The ester 10a, 60 mg (0.217 mmol) was evaporated with toluene twice. It was dissolved in 3.0 mL dry THF and cooled down to −75° C. Under $N_2$ with stirring, DIBAL-H toluene solution 0.68 mL (1.29M, 0.877 mmol) was added dropwise over 20 min. The resulting solution was stirred at −75° C. for another 1.5 h. Then it was allowed to warm up to −5° C. and quenched with 4 mL ethyl acetate. After stirring for 10 min. wet $Na_2SO_4$ (2g) was added. The mixture was stirred at −5° C. for 2 h. The solid was filtered away and washed with ethyl acetate twice. The filtrate was evaporated under reduced pressure. The residue was chromatographed on a silica gel column using 30% (v/v) ethyl acetate-hexane as eluent, yielding pure 11a, 32 mg (63.4%). 11b is obtained the same way from 11b.

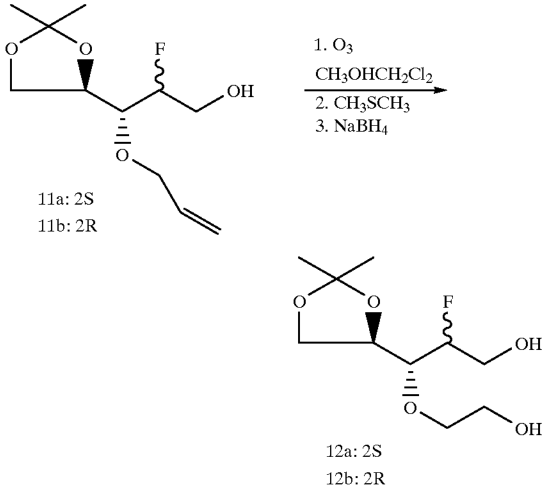

11a: 2S
11b: 2R

12a: 2S
12b: 2R

Compound 11 (a mixture of 11a and 11b), 23 mg (0.099 mmol) was dissolved in 3 mL $CH_3OH$ and 1 mL $CH_2Cl_2$. At −78° C., it was bubbled with $O_3$ until the solution turns bright blue. The solution was then bubbled with argon for 5 min. A drop of dimethyl sulfide was added, and the mixture was stirred for 10 min. Sodium borohydride 30 mg. (0.794 mmol, 8 eq) was added and stirred for 5 min. The reaction mixture was allowed to return to ambient temperature and was stirred for another 1 h. After adding 3 drops of saturated $NH_4Cl$ aqueous solution, the mixture was stirred for another 1 h. The volatiles were removed in vacuo. The residue was dissolved in methanol, and ethyl acetate was added to replace methanol by co-evaporation. The white ppt. was filtered away and the filtrate was evaporated. The residue was chromatographed on a silica gel column using ethyl acetate. After removal of the trace unknown components, 13 mg (55.3%) of 12a and 7 mg (29.8%) of 12b were obtained.

Mesylation and Coupling Reactions

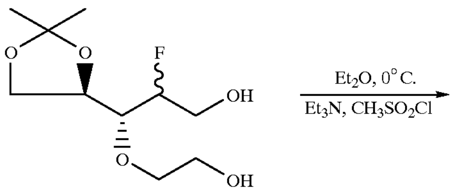

12a: 2R
12b: 2S

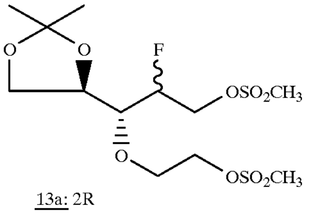

13a: 2R
13b: 2S

The diol (12a), 12 mg (0.050 mmol) was dissolved in 5 mL anhydrous ethyl ether and cooled to 0° C. under $N_2$ atmosphere. Under stirring 35 μL (0.250 mmol, 5 eq.) of $Et_3N$ was added, followed by 20 μL (0.25 mmol, 5 eq.) of mesyl chloride. The resulting mixture was stirred at 0° C. for 5 h. The ppt. was filtered away and washed with ethyl ether. The filtrate was washed with water (2×) and brine (2×) and dried over $Na_2SO_4$. After evaporation of the solvents in vacuo, a yellowish oil 13a, 9 mg (43.3%) was obtained.

The precipitate was dissolved in water and extracted with ethyl acetate. The ethyl acetate layer was washed with $NaHCO_3$ aqueous solution twice and dried over $Na_2SO_4$. After evaporation of the solvent in vacuo, 11 mg (55.3%) of 13a was obtained. Totally 20 mg of 13a was obtained, a 100% yield.

Dimesylate 13a, 20 mg (0.0507 mmol) and bisindolylmaleimide 17.3 mg (0.0507 mmol) were combined and dissolved in 2.5 mL anhydrous DMF (dried over molecular sieves) and added via syringe pump addition to a suspension of cesium carbonate (66 mg. 0.203 mmol in 3 mL anhydrous DMF at 50° C. under $N_2$ over 40 h. The reaction mixture was stirred at 50° C. for another 10 h. It was evaporated in vacuo to remove the volatiles. The residue was dissolved in $CHCl_3$ and washed with saturated $NaHCO_3$ aqueous solution and brine. The chloroform layer was separated and dried over $Na_2SO_4$. After evaporation, the red solid residue was chromatographed on silica gel column with elution of 10% (v/v) acetone/$CHCl_3$. The desired compound 14a, 7 mg (25.4%) was eluted out first, followed by one of the starting material, bisindoyl-maleimide 13 mg (75%).

EXAMPLE 14

Preparation of the bisindolyl maleimide of the formula

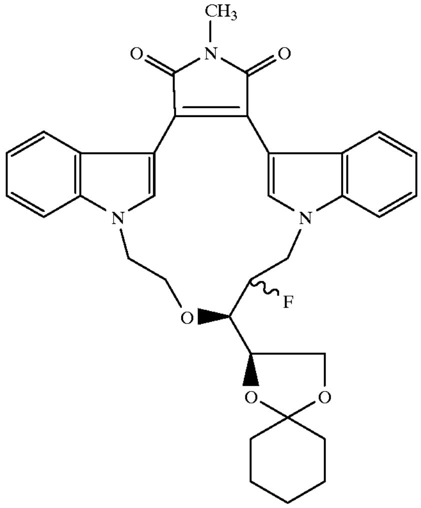

Compounds 21a and 21b are stereoisomers, 21a is in the 2R conformation; 21b is in the 2S conformation. The nomenclature of the chiral center changes when the ester is reduced to the alcohol (i.e. compound 24a becomes 2S).

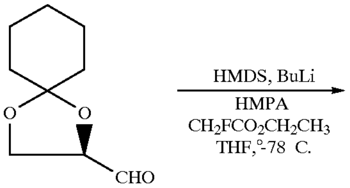

21

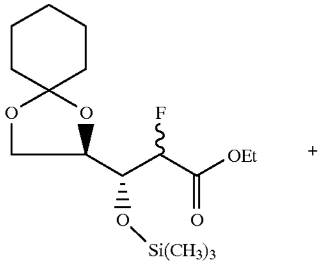

22'

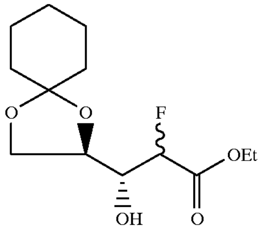

22

To a stirred round-bottomed flask containing 40 mL of anhydrous THF and 5.0 mL (0.0255 mol.) of hexamethyl disilazane 9.0 mL (0.0225 mol) of a 2.5M solution of butyl lithium in hexane was added and reacted in an ice bath under $N_2$. After stirring at room temperature for 10 min, it was cooled to −78° C., and 3.6g (0.020 mol) of HMPA and 2.0 mL (0.020 mol) of ethyl fluoroacetate were added dropwise in 5 min. After stirring for 5 additional min. 760 mg (4.46 mmol) of cyclohexylidene-glyceraldehyde (21, prepared as Ref. JOC, 1992, 57 page 648, and JOC, 1995, 60, pages 585–587, distilled at 60° C./0.5 mmHg) was added quickly. The mixture was allowed to stir for 10 additional min. and then was quenched at −78° C. with 5 mL of saturated ammonium chloride. On warming to room temperature the mixture was diluted with 60 mL hexane. The hexane layer was separated. The remaining layer was extracted with 30 mL hexane. The hexane solutions are combined and washed with saturated ammonium chloride (100 mL×3) and dried over $Na_2SO_4$. After evaporation under reduced pressure, the residue was chromatographed on a silica gel column using 30% ethyl acetate-hexane, yielding the main product 22' 740 mg (47.6%), which is a mixture of two isomers with the major isomer 22'a (74%) and the minor 22'b (26%) based on $^1$HNMR. The aqueous washing was extracted with $CHCl_3$. After evaporation and chromatographing, 92 mg (7.5%) of 21 was obtained from the chloroform layer, which is also a mixture of two isomers. Pure isomer 22'a was obtained from the mixture 22' by chromatography on silica gel column eluted with $CHCl_3$.

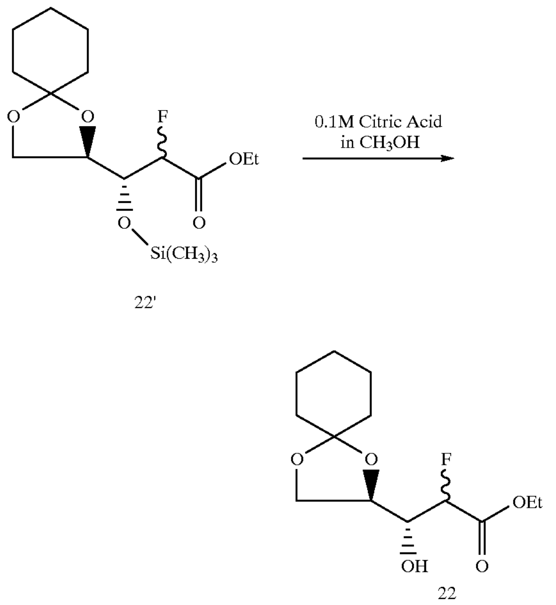

22'

22

The starting material 22', 740 mg (2.1 mmol) was dissolved in 60 ml $CH_3OH$. 1.2 g citric acid was added. The mixture was stirred at ambient temperature for 4 h. The solvent was removed on rotary evaporator. The residue was taken up with ethyl acetate (100 mL) and washed with saturated $NaHCO_3$ aqueous solution (100 mL×2) and water. The ethyl acetate layer was dried over $Na_2SO_4$ and evaporated, yielding 22, 600 mg (100%), which is a mixture of isomer 22a (69%) and 22b (31%) based on $^1$HNMR. Pure 22a was obtained by hydrolysis of 22'a under the same condition producing a 100% yield.

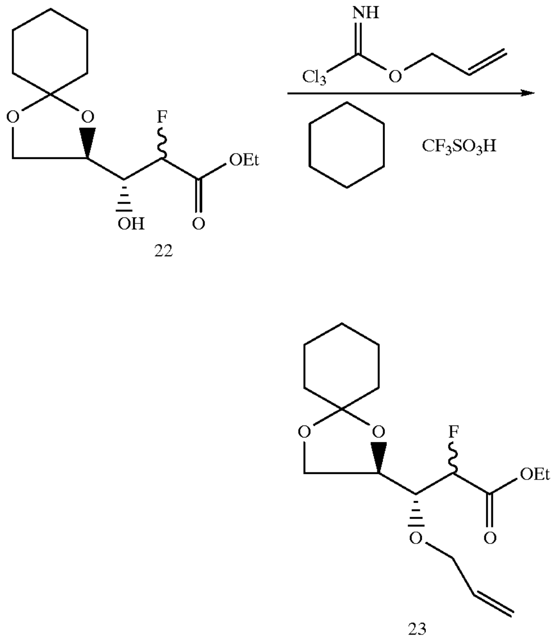

22

23

Alcohol 22, 655 mg (2.37 mmol, a mixture of isomer 21a (69%) and 21b (31%)) was dissolved in 30 mL cyclohexane and 1.50 mL (9.8 mmol) allyl trichloroacetimidate was added. Then 100 μL of $CF_3SO_3H$ was added dropwise over 30 min. The reaction mixture was stirred at ambient temperature under $N_2$ for 46 h. TLC showed that there was about 20% starting material left. Additional 60 μL $CF_3SO_3H$ was added and the reaction mixture was stirred for another 24 h. The ppt. was filtered and washed with cyclohexane. The filtrate was evaporated and the residue was chromatographed on silica gel column using 10% ethyl acetate-hexane as eluent, yielding 23a, 511 mg (68.1%) and 23b, 160 mg (21.3%).

Pure 23a is also obtained from pure 21a using the same condition above for comparison.

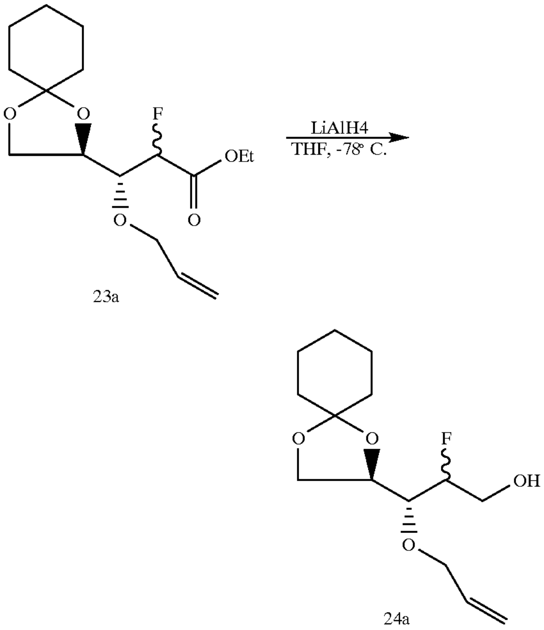

23a

24a

The ester 23a, 635 mg (2.00 mmol) was evaporated with toluene twice and dissolved in 10 mL anhydrous THF. It was dropwise added to a suspension of 200 mg (5.27 mmol, 2.5 eq.) $LiAlH_4$ in 40 mL anhydrous THF at −78° C. under $N_2$ with stirring. After adding the sample, the reaction mixture was stirred for 20 min. It was warmed up to 0° C. and stirred at 0° C. for 20 min. Then 5 mL ethyl acetate was added. After stirring for 5 min., 4 g wet sodium sulfate was added. The mixture was stirred for 30 min. The solid was filtered away and washed with ethyl acetate twice. The filtrate was evaporated on rotary evaporator. The residue was chromatographed on a silica gel column using 30% ethyl acetate/hexane as eluent. After removing some starting material 23a, 19 mg, the main product was eluted out, as 24a, 413 mg (75.0%), followed by some 24b, 30 mg (5.5%).

Compound 24b (44 mg) was obtained by reduction of 23b (112 mg) using DIBAL-H in THF using a similar procedure as above, with 45% yield.

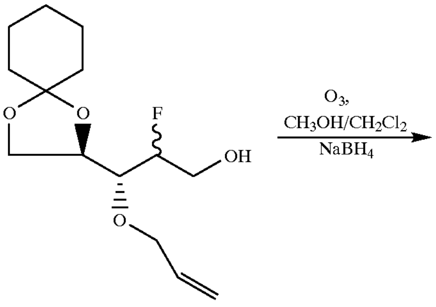

24a

-continued

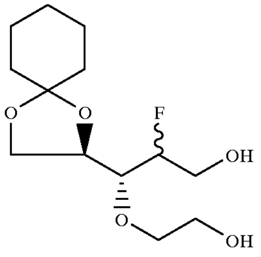

25a

The alcohol 24a, 295 mg (1.08 mmol) was dissolved in 20 mL mixture solvent of $CH_3OH/CH_2Cl_2$ (1:1). It was cooled down to −78° C. Ozone was bubbled through until a blue color began to appear. Argon then was bubbled in to exclude excess 03. Several drops of $CH_3SCH_3$ was added and the solution was stirred for 5 min. Then 245 mg (6.48 mmol) of $NaBH_4$ was added at −78° C. After stirring for 5 min., the reaction mixture was allowed to return to ambient temperature and stirred for 1 h. The volatiles were removed in vacuo. The residue was chromatographed on silica gel column using ethyl acetate as eluent, yielding 25a, 232 mg (77.5%)

The diol 25b was obtained following the same procedure above. The reaction was initiated with 230 mg of 24b, and 158 mg of 25b was obtained with a yield of 67.7%.

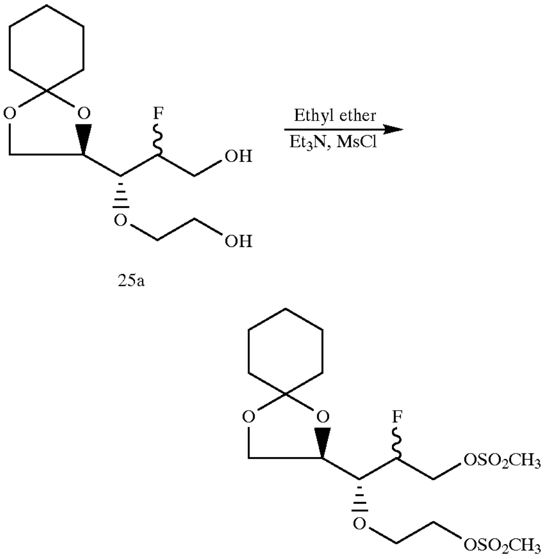

25a

26a

Diol 25a, 195 mg (0.70 mmol) was dissolved in 50 mL diethyl ether. Triethyl amine 583 μL (4.2 mmol) was added and followed by 342 μL (4.2 mmol) of methanesulfonyl chloride. The mixture was stirred at ambient temperature under $N_2$ for 3 h. 50 mLs of water, was added to dissolve the ppt. The ether layer was separated and washed with water (50 mL×2). After drying over anhydrous $Na_2SO_4$, it was evaporated at reduced pressure to yield a yellowish liquid 26a, 308 mg (100% ).

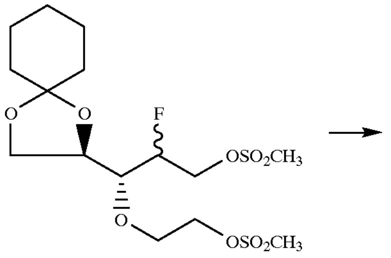

26a

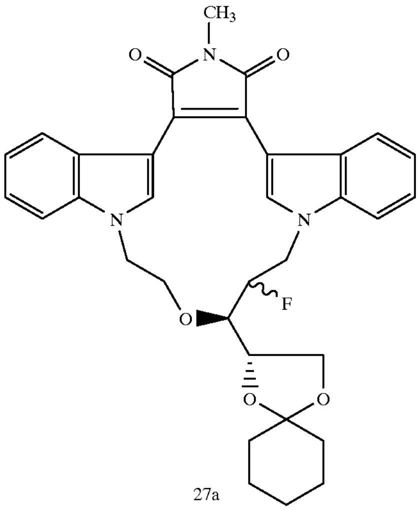

27a

To a 100 mL round-bottomed flask containing 768 mg (2.36 mmol) cesium carbonate in 40 mL anhydrous DMF at 50° C. under $N_2$, 10 mL of DMF solution containing 26a, 257 mg (0.59 mmol) and bisindolylmaleimide, 202 mg (0.59 mmol) was added dropwise via a syringe pump over a period of 48 h. After stirred at 50° C. for additional 24 h, the reaction mixture was diluted with 100 mL $CHCl_3$ and washed with brine (50 mL×2), then water (50 mL×2). The chloroform layer was dried over anhydrous $Na_2SO_4$ and evaporated under reduced pressure. The residue was dissolved in $CHCl_3$ and chromatographed on silica gel column using 5% acetone/$CHCl_3$ as eluent. The first component eluted out is the desired product 27a, 185 mg. It was recrystallized from $CHCl_3/CH_3OH$, yielding 130 mg (37.7%) and a filtrate.

Compound 27b was obtained in the same way as above, except that the addition time of the mesylate and bis indolyl maleimide via a syringe pump was 80 h. The reaction was initiated with 97 mg of the diol 25b, and 64 mg of 27b was obtained with an overall yield of 26.1%.

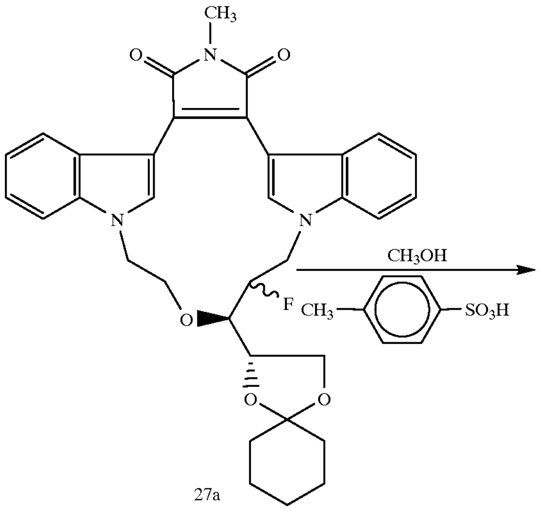

27a

-continued

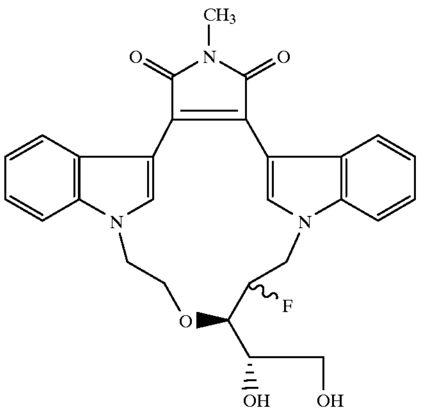

28a

The starting material 27a, 50 mg (0.099 mmol) was dissolved in 50 mL methanol. To it 1 mL water and 200 mg of p-toluene-sulfonic acid monohydrate (1.05 mmol) were added. The reaction mixture was stirred at 50° C. for 4 h. It was evaporated on rotary evaporator and the residue was chromatographed on silica gel column using 5% $CH_3OH/CHCl_3$ as eluent. The main component 28a was recrystallized from acetone/$CH_3OH$, yielding crystalline 28a, 23 mg and a filtrate which contains 18 mg of 28a (95.0%).

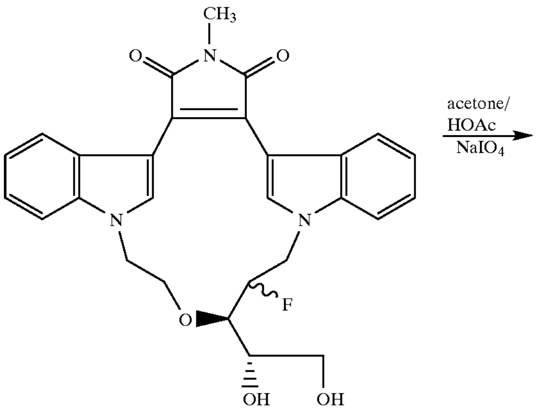

28a

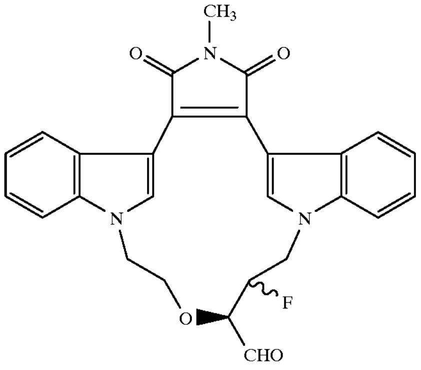

29a

Diol 28a, 55 mg (0.109 mmol) was dissolved in 20 ml of acetone-HOAc mixture (1:1). To the solution, 100 mg of $NaIO_4.3H_2O$ (0.373 mmol) in 2.5 ml water was added. The mixture was stirred at ambient temperature for 2.5 h. It was evaporated on a rotoevaporator to reduce solution volume to half, and then diluted with 30 ml $CH_2Cl_2$. The mixture was then washed with water twice, aqueous $NaHCO_3$ and water again. The $CH_2Cl_2$ layer was separated, dried over $Na_2SO_4$ and evaporated to dryness, yielding crude aldehyde 29a.

The crude aldehyde 29a was dissolved in 14 ml $CH_2Cl_2$ and cooled to −78° C. Sodium borohydride, 30 mg (0.79 mmol) was dissolved in 6 ml of SP reagent alcohol and added to the solution. The mixture was stirred under $N_2$ for 40 min. It was quenched with 500 μl $CH_3CHO$ and then allowed to return room temperature. The mixture was evaporated to reduce the solution volume to half and then mixed with 10 ml $C_2H_5OH$, 2 ml of Potassium Sodium tartrate saturated aqueous solution. The mixture was stirred for 5 h. It was evaporated and taken up with 30 ml $CH_2Cl_2$. The $CH_2Cl_2$ layer was separated, washed with water three times and dried over $Na_2SO_4$. After evaporation, the residue was chromatographed on a silica gel column using 10% ethyl acetate in $CH_2Cl_2$, yielding compound 30'a, 7 mg (14.1%). The main component was eluted with ethyl acetate, yielding the desired product 30a, 41 mg (79.3%).

Compound 30b was obtained from the corresponding diol 28b (with a yield of 63.4%) following the same procedure as above except that the solvent for the cleavage of the diol was a mixture of $CH_3CN—H_2O$ (2:1).

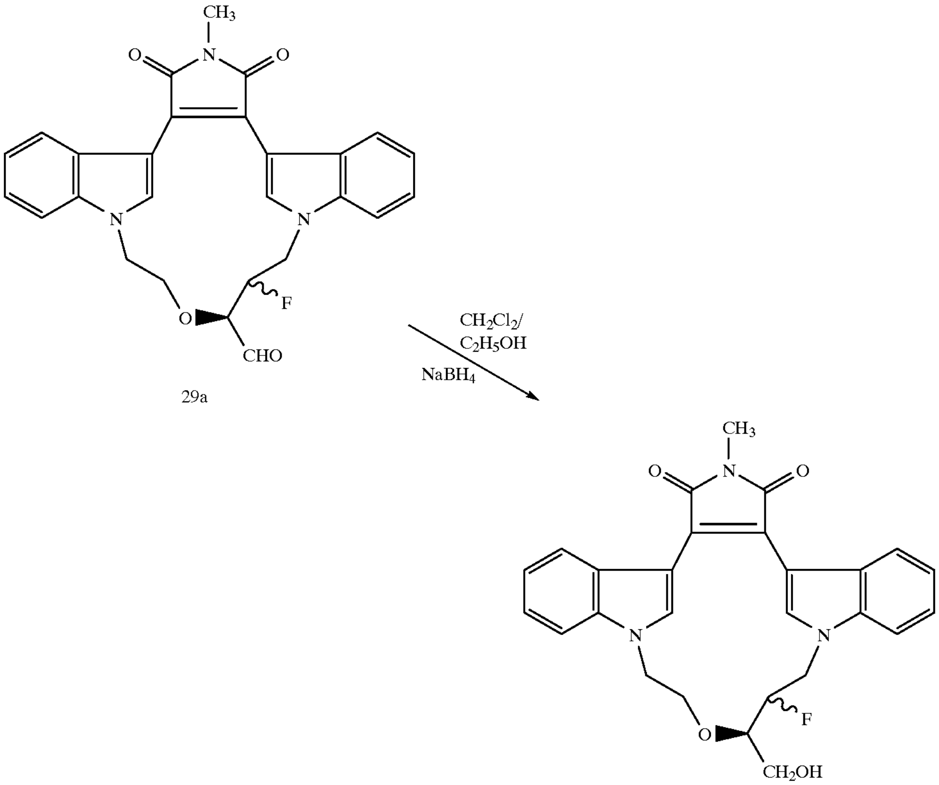
29a
30a
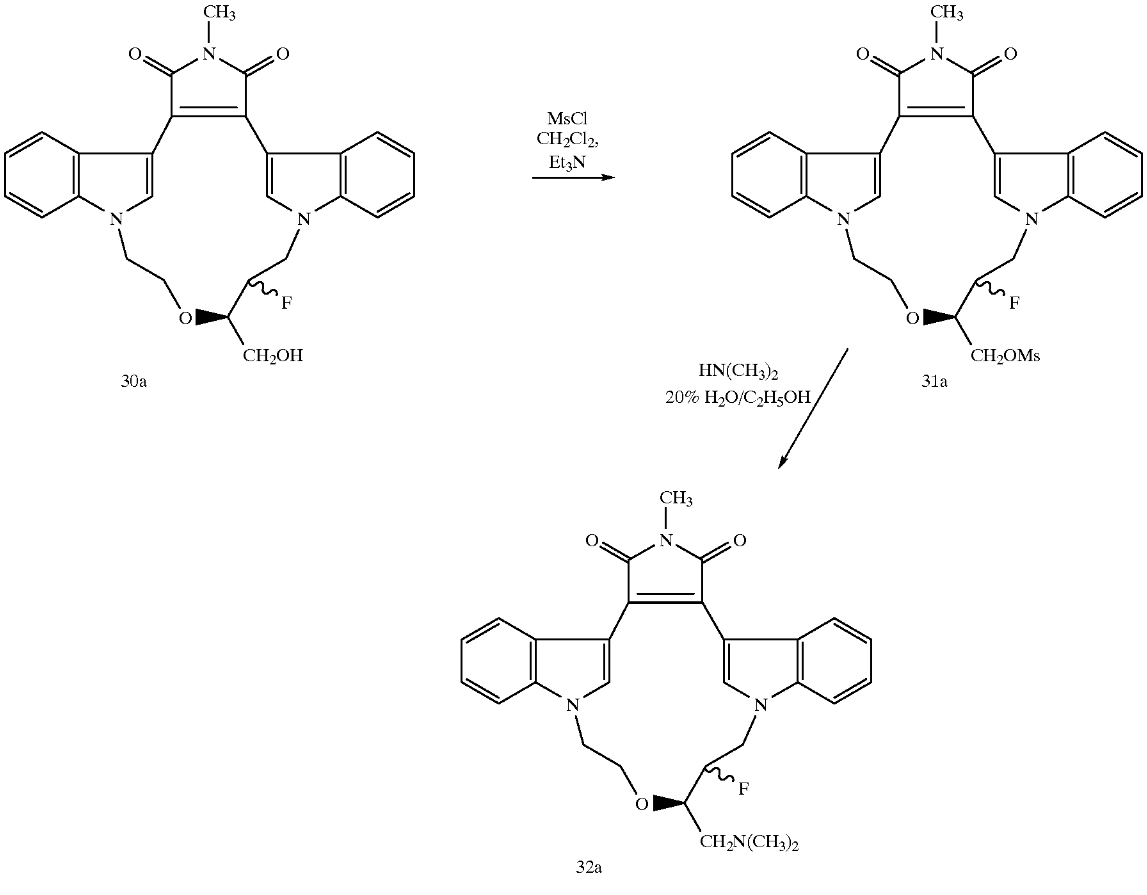
30a
31a
32a

The alcohol 30a, 16 mg (0.0338 mmol) was dissolved in 10 mL $CH_2Cl_2$. To it 70 $\mu$L (0.52 mmol) of triethylamine and 28 $\mu$L (0.34 mmol) of methanesulfonyl chloride were added. The reaction mixture was stirred at ambient temperature under $N_2$ for 3 h. It was transferred to a separatory funnel and washed with water three times. After evaporation it yields crude 31a, 23 mg. TLC shows only one spot.

The crude mesylate 31a, 23 mg (~0.0338 mmol) was placed in a 25 mL-round-bottomed flask and 12 mL $C_2H_5OH$ was added. The flask was cooled down using dry ice/acetone bath. Into it 1.2 g $HN(CH_3)_2$ and 3 mL water were transferred via cannula. The flask was then sealed with a teflon stopper and tied using copper wire, It was stirred at 100° C. for 8 h. After the flask cooled to room temperature, the volatiles were removed on rotary evaporator. The residue was dissolved in 20 mL ethyl acetate and washed with aqueous $NaHCO_3$ (20 mLx2), water (20 mLx2). After removing solvent it yields 24 mg crude produce 32a which was recrystallized from methanol, obtaining pure 32a.

The imide 32a, 24 mg (0.048 mmol) was dissolved in a mixture of 3 mL $C_2H_5OH$ and 3 mL 5N KOH. It was stirred at 80° C. for 24 h. The ethanol was removed on rotary evaporator and the aqueous suspension was cooled to 0° C. and acidified with 5N HCl. A violet precipitate appears. After stirring for 10 min., the aqueous mixture was neutralized with dilute KOH and extracted with ethyl acetate. The ethyl acetate layer was washed with aqueous $NaHCO_3$ twice and water. After drying over $K_2CO_3$ and evaporation, it yields 24 mg crude 33a.

The anhydride 33a, 24 mg was dissolved in 5 mL anhydrous DMF. To it 250 $\mu$L(1.19 mmol 1,1,1,3,3,3-hexamethyl disilazane was added, followed by adding 25 $\mu$L $CH_3OH$ (0.62 mmol). The resulting mixture was stirred at ambient temperature under $N_2$ for 38 h. The volatiles was removed in vacuo. The residue was dissolved in 6 mL mixture solution of $CH_3CN$–1NHCl (2:1) and stirred at ambient temperature for 1 h. The organic solvent was removed and the aqueous suspension was neutralized with 1N KOH and extracted with ethyl acetate. The ethyl acetate layer was washed with 0.1N KOH and water twice and evaporated to dryness. The residue was separated on silica gel column eluted with ethyl acetate. The second band eluted out is the desired product 14*a* which was recrystallized from $CH_2Cl_2$-hexane, yielding 5 mg (overall yield from 30a, 20%).

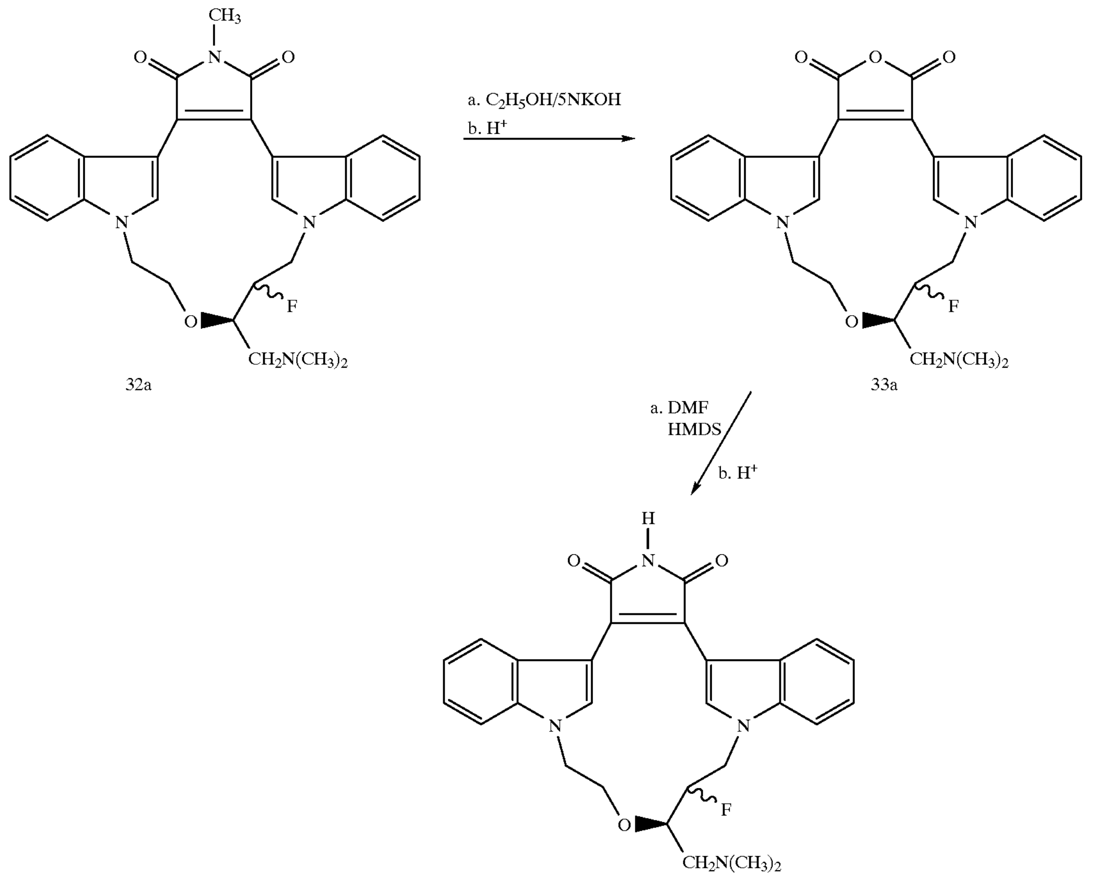

32a 33a 34a

EXAMPLE 15

Alternative Scheme for Producing Compounds 34(a and b) from Compounds 30 (a and b).

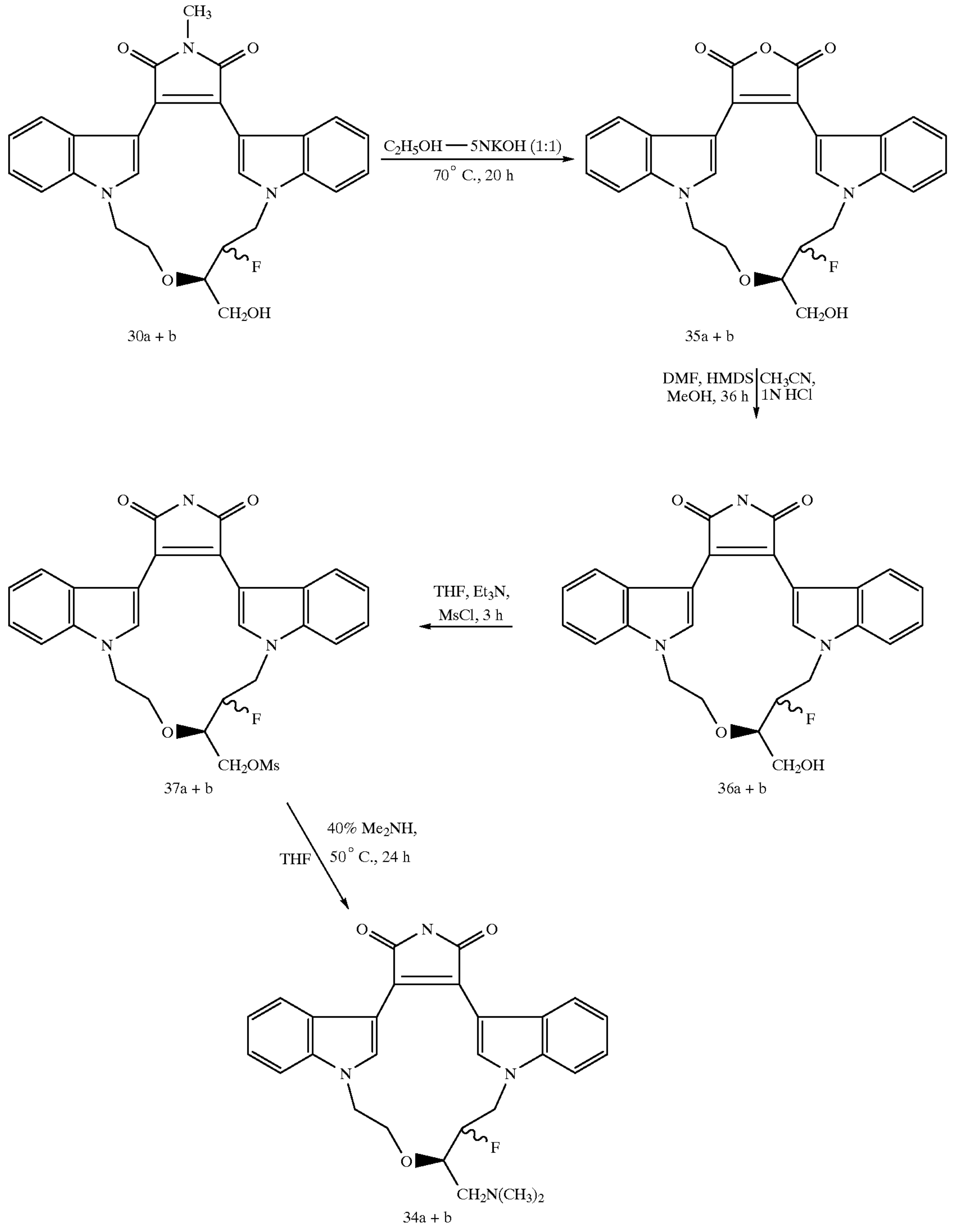

Alcohol 30a, 50 mg (0.106 mmol) was mixed with 20 ml of $C_2H_5OH$–5N KOH (1:1). It was stirred at 70° C. under $N_2$ for 20 h. It then was cooled to 0° C. and acidified with 5N HCl. Red ppt immediately appeared. Methylene chloride, 40 ml, was added. The organic layer was separated and washed with water (30 ml×4), and dried over $Na_2SO_4$. After evaporation, the residue was chromatographed on a silica gel column using 5% ethyl acetate in $CH_2Cl_2$, yielding 35a, 33 mg (68%).

The anhydride 35a, 54 mg (0.117 mmol) was dissolved in 5 ml anhydrous DMF. HMDS (1, 1, 1, 3, 3, 3-hexamethyl disilazane). 500 μl (2.36 mmol) and methanol, 48 μl (2.36 mmol) were added. The mixture was stirred under $N_2$ at ambient temperature for 36 h. The volatiles were removed in vacuo and the residue was stirred with 10 ml $CH_3CN$ and 5 ml IN HCl for 1 h. It was then concentrated and extracted with $CH_2Cl_2$. The methylene chloride layer was washed with water, brine, dried over $Na_2SO_4$, and evaporated. The residue was separated on a silica gel column using $CH_2Cl_2$—$CH_3CN$ (9:1), yielding the first component which was the starting material (20 mg, 37.0%), then the desired product at 36*a*, 31 mg (57.4%).

Compound **36*b*, 3.4 mg (39%) was obtained from corresponding alcohol 30b, 9 mg (0.019 mmol) following the same procedure as above except that far more excess of HMDS (250 μl, 1.18 mmol) and methanol (24 μl, 1.18 mmol) was used than that for 36***a*. *Amination:*

Compound 36a, 31 mg (0.068 mmol) was dissolved in 15 ml anhydrous THF. To it 240 μl (1.56 mmol) of triethylamine and 84 μl (1.02 mmol) of methane sulfonyl chloride were added under nitrogen atmosphere. The mixture was stirred at ambient temperature for 3 h. The volatiles were removed in vacuo. The residue was dissolved in 30 ml $CH_2Cl_2$ and washed with 1NHCl, brine twice, dried over $Na_2SO_4$ and evaporated. The residue was dissolved in 6 ml of distilled THF and 1 ml of 40% dimethylamine in water. The flask was sealed with a Teflon stopper and stirred at 50° for 24 h. The mixture was cooled to 0° C. and evaporated to remove the volatiles. The residue was purified on silica gel column using 0–10% $Et_3N$ in ethyl acetate, yielding the desired compound 34a, 13.2 mg (40.2%).

Compound 34b (1.9 mg) was obtained from 36b (3.4 mg) using the same procedure as for 34a with a yield of 52%.

EXAMPLE 16

Synthesis of a Dithiocarbamate Derivative

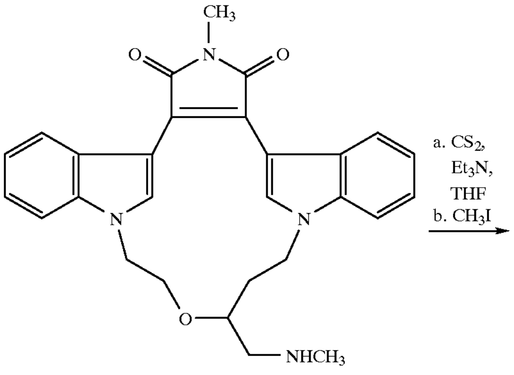

38

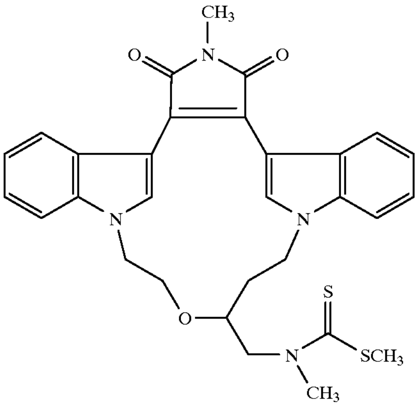

39

20 mg of Compound 38 (0.04 mmol, 1 eq.) was transferred to an oven dried 25 mL round bottom flask equipped with stir bar, septum, and $N_2$ balloon. 10μl of THF was added via canula followed by 4.45 mg of triethylamine (0.044 mmol,1.1 eq.) and then 3.8 mg carbon disulfide (0.05 mmol,1.2 eq.) via syringe. This red solution was allowed to stir for ~15 min. and then 7.1 mg of methyl iodide (0.05 mmol, 1.2 eq.) was added via syringe. The reaction was allowed to stir at room temp overnight.

The clear red solution turned cloudy after approximately two hours. TLC (10% MeOH in $CH_2Cl_2$) showed total loss of starting material. The reaction was transferred to a separatory funnel with EtoAc and washed with 40 mL of $H_2O$ followed by 40 mL of brine. The organic layer was collected and passed through $MgSO_4$ in a sintered glass funnel to dry it. The solvent was removed to give a purple solid (compound 39). A sample was analyzed by IS/MS. The IS/MS detected a MH+peak at 559, total yield was 23 mg.

Conversion of the Dithiocarbamate to Trifluoromethyl Group

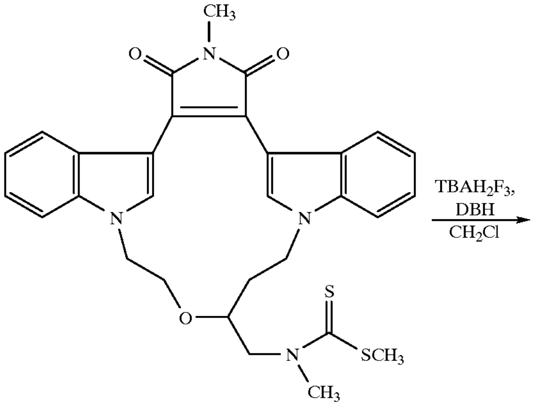

39

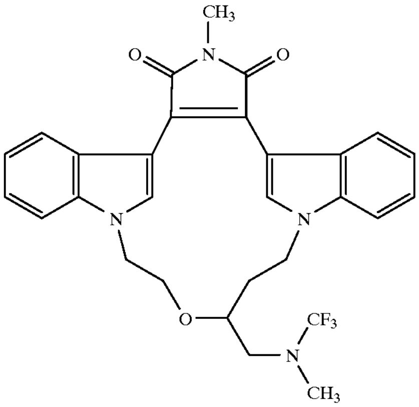

40

The 23 mg (0.041 mmol,1eq.) of dithiocarbamate 39 was dissolved in anhydrous $CH_2Cl_2$ in a dry 25 ml round bottom flask equipped with stir bar, septum, and $N_2$ balloon. The solution was cooled in an ice bath for about 15 min. 0.047g 1,3-dibromo 5,5- dimethylhydantoin (0.164 mmol, 4 eq.) was then added quickly as a solid followed by 0.06 g of tetrabutylammonium dihydrogentriflouride (0.205 mmol, 5eq.) via syringe. (The solution went from reddish/purple to an orange/brown color).

The reaction was stirred at 0° C. for 1.5 hrs. It was then dumped into a separatory funnel filled with 30 mL $H_2O$. The $CH_2Cl_2$ layer was washed again with 25 ml $H_2O$, collected, and derived over $MgSO_4$. The solvent was removed to give a dark brown/orange oil. The product was purified through the use of a silica gel, starting with $CH_2Cl_2$ as the mobile phase and gradually adding methanol. Three separate spots were obtained, the third sample was collected, and the solvent was removed to yield 16.5 mg (75%) of product 40.

EXAMPLE 17

Acylation of the amine of Compound A

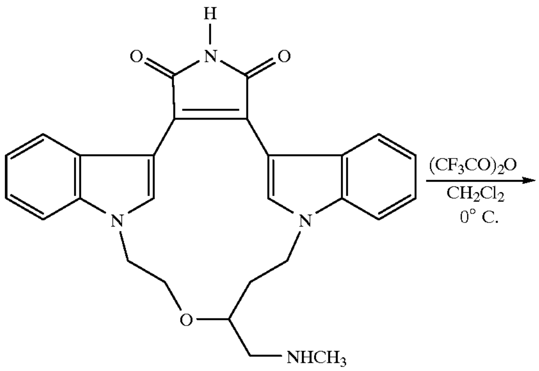

A

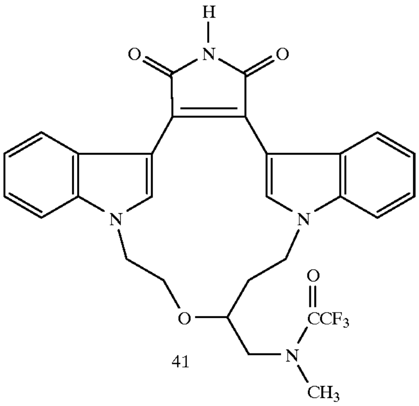

41

7 mg (0.0154 mmol) of Compound A was dissolved in 1 mL dry $CH_2Cl_2$. It was cooled to 0° C. under $N_2$, and stirred while 3.7 μL (0.046 mmol, 3eq) of pyridine was added, followed by 2.06 μL (0.018 mmol, 1.2 eq.) of trifluoroacetic anhydride (Aldrich). The reaction mixture was stirred at 0° C. from 2:17 p.m. to 4:20 p.m. (TLC 1) and continued until 7:00 p.m. (TCL 2). No more progress of the reaction. Another batch of 3.7 μL pyridine and 2.6 μL trifluoroacetic anhydride were added. After stirring for 4 h, TLC shows no significant progress of the reaction. The reaction mixture was allowed to warm up to room temperature and stirred for 3 h. Again, TLC shows no significant progress of the reaction. A third batch of 3.7 μL pyridine and 2.0 mL of trifluoro acetic anhydride was added the mixture was stirred for 2 h, TLC shows the conversion is improved.

The reaction was stopped and the volatiles were evaporated under reduced pressure. The residue was dissolved in $CHCl_3$ and washed with saturated $NaHCO_3$ aq. solution and water, twice, and the $CHCl_3$ layer was evaporated. The residue was chromatographed on a silica gel column eluted with 10% acetone-$CHCl_3$ (v/v) obtaining two pure components, 208.1 and 208.2. The starting material remaining in the column was eluted with 10% $CH_3OH$—$CHcl_3$ containing 2% $Et_3N$, labeled as 208.3.

208.1~1 mgRf=0.67

208.2~3 mgRf=0.45

208.3~4 mgRf=0

$^1$HNMR in $CDC1_3$ 208.2 file: GZW.013 (Dept. 3): —N—$CH_{3,\ \delta 3.10}$ ppm.

208.3 file: GZW.014 (Dept.3) : —N—$CH_{3,\ \delta 2.40}$ ppm.

In $CDCl_3$ the methyl-group signal shows a significant low field shift from δ2.40 ppm to δ3.10 ppm. Therefore the desired product is the product 2 (compound 41).

The experiment was repeated as described below:

A collection of recovered material 208.1, ~5 mg. (0.011 mmol) was co-evaporated with toluene twice and dissolved in 2 mL dry $CH_2Cl_2$ (over molecular sieve). 40 μL pyridine (0.497 mmol, 45 eq.) was added at 0° C., followed by 10 μL (0.071 mmol. 6.5 eq.) of $(CF_3CO)_2O)$ . The mixture was stirred under $N_2$ for 2 hr TLC 1 showed reaction was complete. The volatiles were evaporated in vacuo and the residue was passed through a tiny silicon gel column using 10% acetone —$CHCl_3$ as eluent, yielding 5 mg product labeled as 209–2.

EXAMPLE 18

Preparation of the bisindolyl maleimide of the formula

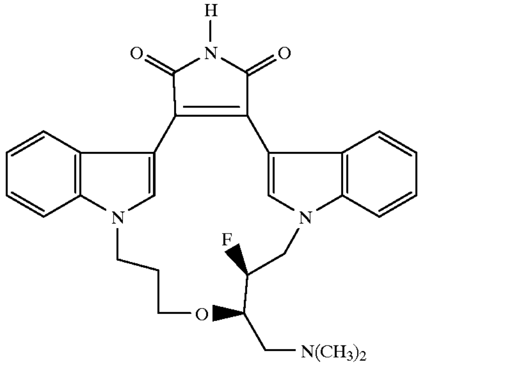

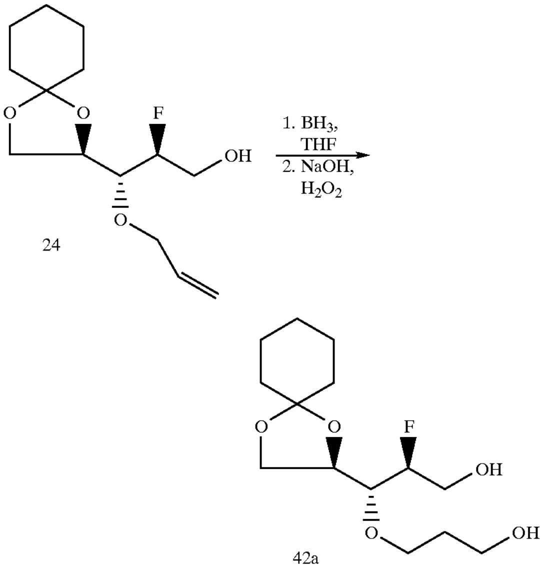

24

42a

Compound 24a, 140 mg (0.511 mmol) was evaporated with toluene twice and dissolved in 5.0 ml of freshly distilled anhydrous THF. It was cooled to 0° C. (ice bath) and stirred under $N_2$. To it 5.0 ml (5.0 mmol) of 1.0M solution of $BH_3$.THF in THF was added via a syringe. The resulting mixture was allowed to warm up slowly to room temperature and stirred under $N_2$ for 15 h. It was cooled with an ice-bath and then 10 ml of 10% NaOH was added, followed by addition of 10 ml of 50% $H_2O_2$. The resulting white cloudy mixture was stirred at room temperature for 5 h. It was evaporated on a rotoevaporator to remove THF and the residue was diluted with 50 ml water. It was extracted with ethyl acetate (40 ml.x3). The ethyl acetate layer was washed with brine (50 ml) and dried over $Na_2SO_4$. After evaporation the residue was separated on a silica gel column (1 cm×12.5 cm, flash chromatography) using toluene (20 ml), 30%–100% ethyl acetate in hexane (145 ml). The fourth component was identified to be the desired produce 42a, 69 mg (46%).

Compound 49 was synthesized using the following steps and the same general procedure as discussed in detail in Example 14.

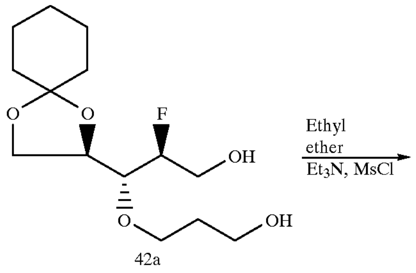

42a
130 mg (0.445 mmol)

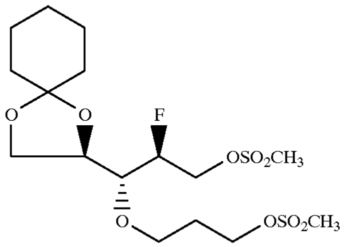

43a
197 mg (98.8%)

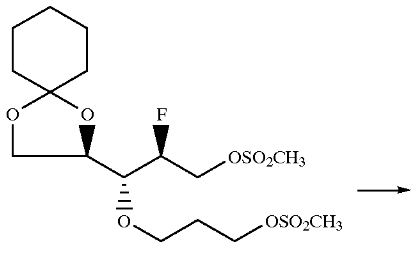

43a
190 mg (0.44 mmol)

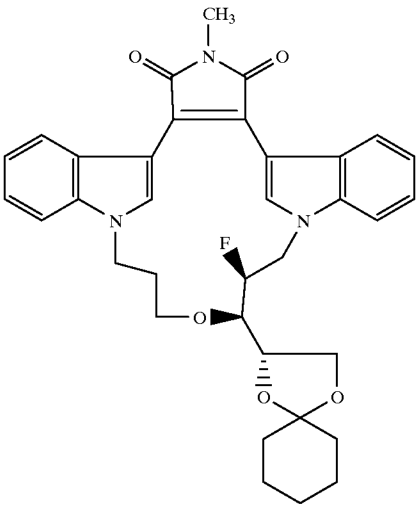

44a
125 mg (47.5%)

-continued 44a
74 mg (0.12 mmol)

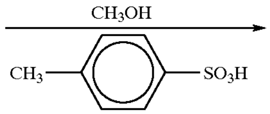

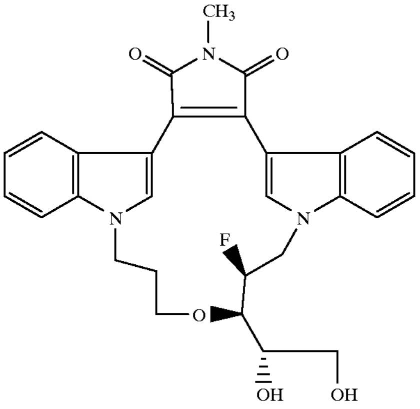

45a
51 mg (0.99 mmol, 80%)

45a
51 mg
(0.099 mmol)

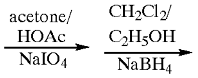

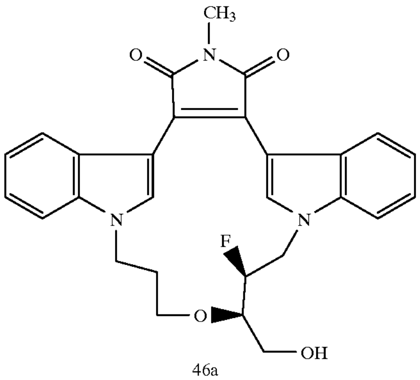

46a
46 mg (0.094 mmol, 95%)

46a
46 mg (0.094 mmol)

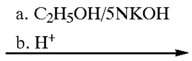

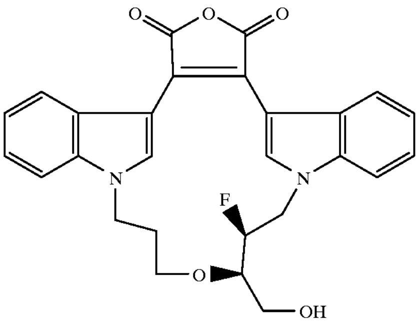

47a
36 mg (0.076 mmol. 81%)

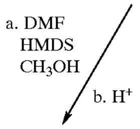

-continued

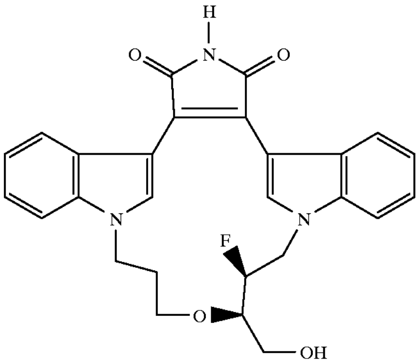

48a 20 mg (0.043 mmol, 56%)

48a

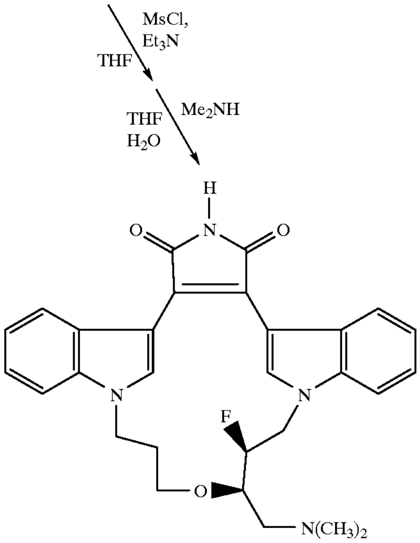

49a

EXAMPLE 19

Protein Kinase C Inhibition In Vitro Assay

Reaction Mixture:

10 μl $Ca^{2++}$ (9.4 mM stock)

55 μl lipids (PS 5 μg/well, DG 0.6 μg/well) or HEPES

5 μl Compound or DMSO (Test compounds initial concentration at 5000 nM

10 μl Myelin Basal Protein (MBP) Substrate (MBP 3 mg/ml, lot# 451–026)

10 μl ATP (300 μM ATP, 0.25 μCi/well $AT^{32}P$, and 10 μl Enzyme (PKC α 1:80 in HEPES, $\beta_{II}$ 1:30, in HEPES)

HEPES buffer stock is 100 mM, pH 7.5.

The total Reaction Mixture equaled 100 μl and was incubated for 10 minutes at 30° C. The reaction was stopped with the addition of 100 μl 25% TCA. 25 μl of a 1 mg/ml BSA solution was added and 200 μl of the reaction mixture was transferred to a 96-well glass fiber filtration plate (Millipore Cat.# MAFCNOB50). The supernatant was filtered and washed three times with 10% TCA. The bottom of the filtration plate and the installed carrier was removed. 100 μl of Microscint-20 (Packard Cat.# 6013621) was added and the samples were loaded onto a Packard topcounter.

Lipid Preparation

Lipids (Avanti Polar Lipids) were added to a borosilicate glass culture tube (25×150 mm). The lipids were dried under nitrogen until the chloroform was evaporated. The lipids were resuspended in HEPES buffer, and sonicated for approximately 30 seconds, then vortexed to mix well. Lipids were kept on wet ice until the addition to the assay.

Results

The $IC_{50}$ values were determined for each of the following compounds, using the above in vitro assay. Five concentrations of each compound were tested against PKC alpha (PKC α) and PKC beta II (PKC $\beta_{II}$). The concentrations of the tested compounds were 5000 nM, 500 nM, 50 nM, 5 nM, 1 nM and zero (no compound, DMSO only). The sample without any added compound was used to determine 100% activity of the PKC enzyme in the assay. The $IC_{50}$ values were estimated from the inhibition curves employing these concentrations.

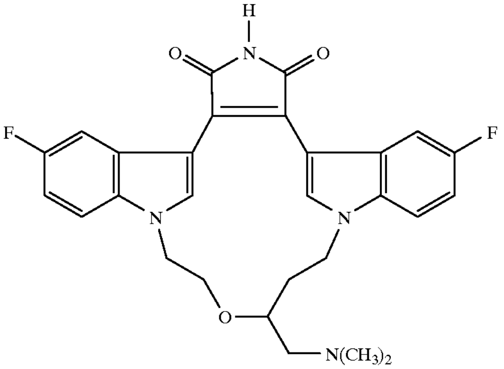

$IC_{50}$ Values in nanoMolar (nM)

| PKC α | PKC $\beta_{II}$ |
|---|---|
| 57 | 5.0 |

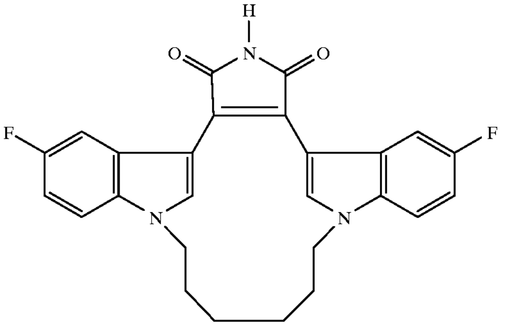

$IC_{50}$ Values in nanoMolar (nM)

| PKC α | PKC $\beta_{II}$ |
|---|---|
| 79 | 5.5 |

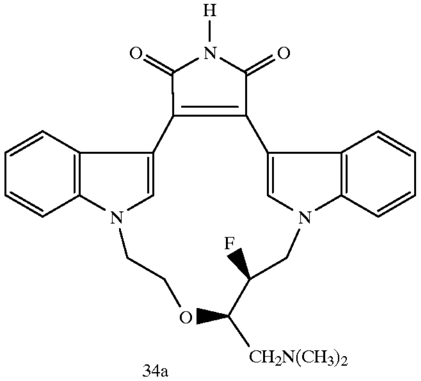

34a

-continued

IC50 Values in nanoMolar (nM)

PKC α PKC β II 140 3.5

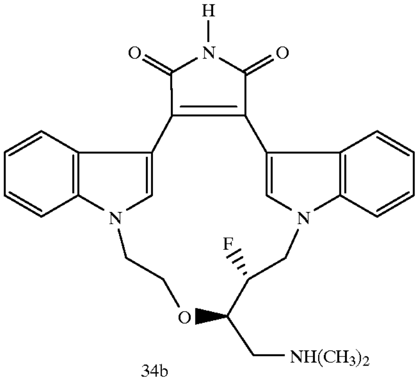

34b

IC50 Values in nanoMolar (nM)

PKC α PKC β II 26 2.4

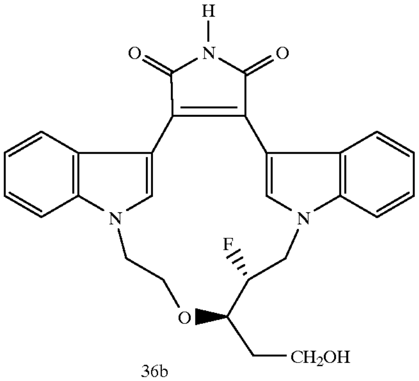

36b

IC50 Values in nanoMolar (nM)

PKC α PKC β II 2.6 2.2

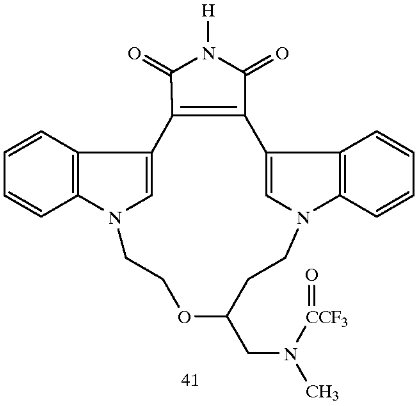

41

IC50 Values in nanoMolar (nM)

PKC α PKC β II 2700 100

-continued

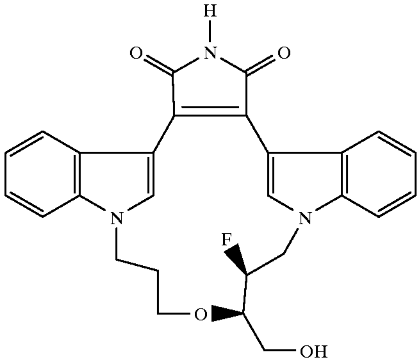

48a

IC50 Values in nanoMolar (nM)

PKC α PKC β II 130 13

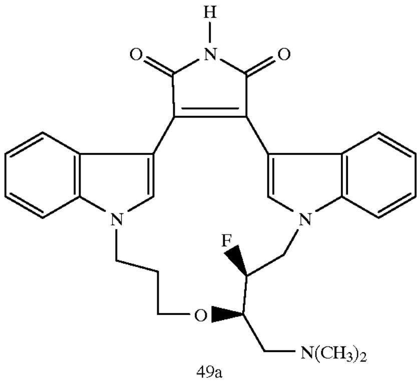

49a

IC50 Values in nanoMolar (nM)

PKC α PKC β II 1300 90

As an inhibitor of protein kinase C, the compounds disclosed herein are useful in the treatment of conditions in which protein kinase C has demonstrated a role in pathology. Conditions recognized in the art include: diabetes mellitus and its complications, ischemia, inflammation, central nervous system disorders, cardiovascular disease, Alzheimer's disease, dermatological disease and cancer.

Protein kinase C inhibitors have been shown to block inflammatory responses such as neutrophil oxidative burst, CD3 down-regulation in T-lymphocytes, and phorbol-induced paw edema. Twoemy, B. et al. *Biochem. Biophys. Res. Commun.* 171: 1087–1092 (1990); Mulqueen, M. J. et al. *Agents Actions* 37: 85–89 (1992). Accordingly, as inhibitors of PKC, the present compounds are useful in treating inflammation.

Protein kinase C activity plays a central role in the functioning of the central nervous system. Huang, K. P. *Trends Neurosci.* 12: 425–432 (1989). In addition, protein kinase C inhibitors have been shown to prevent the damage seen in focal and central ischemic brain injury and brain edema. Hara, H. et al. *J. Cereb. Blood Flow Metab.* 10: 646–653 (1990); Shibata, S. et al. *Brain Res.* 594: 290–294 (1992). Recently, protein kinase C has been determined to be implicated in Alzheimer's disease. Shimohama, S. et al., *Neurology* 43: 1407–1413 (1993). Accordingly, the compounds of the present invention are useful in treating Alzheimer's disease and ischemic brain injury.

Protein kinase C activity has long been associated with cell growth, tumor promotion and cancer. Rotenberg, S. A. and Weinstein, I. B. *Biochem. Mol. Aspects Sel. Cancer* 1: 25–73 (1991). Ahmad et al., *Molecular Pharmacology:* 43: 858–862 (1993). It is known that protein kinase C inhibitors are effective in preventing tumor growth in animals. Meyer, T. et al. Int. *J. Cancer* 43: 851–856 (1989); Akinagaka, S. et al. Cancer Res. 51: 4888–4892 (1991). The compounds of the present invention also act as multidrug reversal (MDR) agents making them effective compounds when administered in conjunction with other chemotherapeutic agents.

Protein kinase C activity also plays an important role in cardiovascular disease. Increased protein kinase C activity in the vasculature has been shown to cause increased vasoconstriction and hypertension. A known protein kinase C inhibitor prevented this increase. Bilder, G. E. et al. *J. Pharmacal. Exp. Ther.* 252: 526–530 (1990). Because protein kinase C inhibitors demonstrate inhibition of the neutrophil oxidative burst, protein kinase C inhibitors are also useful in treating cardiovascular ischemia and improving cardiac function following ischemia. Muid, R. E. et al. *FEBS Lett.* 293: 169–172 (1990); Sonoki, H. et al. *Kokyu-To Junkan* 37: 669–674 (1989). The role of protein kinase C in platelet function has also been investigated and as shown elevated protein kinase C levels being correlated with increased response to agonists. Bastyr III, E. J. and Lu, *J. Diabetes* 42: (Suppl. 1) 97A (1993). PKC has been implicated in the biochemical pathway in the platelet-activity factor modulation of microvascular permeability. Kobayashi etal., *Amer. Phys. Soc. H*1214–H1220 (1994). Potent protein kinase C inhibitors have been demonstrated to affect agonist-induced aggregation in platelets. Toullec, D. et al. *J. Biol. Chem.* 266: 15771–15781 (1991). Protein kinase C inhibitors also block agonist-induced smooth muscle cell proliferation. Matsumoto, H. and Sasaki, Y. *Biochem. Biophys. Res. Commun.* 158: 105–109 (1989). Therefore, the present compounds are useful in treating cardiovascular disease, atherosclerosis and restenosis.

Abnormal activity of protein kinase C has also been linked to dermatological disorders such as psoriasis. Horn, F. et al. *J. Invest Dermatol.* 88: 220–222 (1987); Raynaud, F. and Evain-Brion, D. *Br. J. Dermatol.* 124: 542–546 (1991). Psoriasis is characterized by abnormal proliferation of keratinocytes. Known protein kinase C inhibitors have been shown to inhibit keratinocyte proliferation in a manner that parallels their potency as PKC inhibitors. Hegemann, L. et al. *Arch. Dermatol. Res.* 283: 456–460 (1991); Bollag, W. B. et al. *J. Invest. Dermatol.* 100: 240–246 (1993). Accordingly, the compounds as inhibitors of PKC are useful in treating psoriasis.

Protein kinase C has been linked to several different aspects of diabetes. Excessive activity of protein kinase C has been linked to insulin signaling defects and therefore to the insulin resistance seen in Type II diabetes. Karasik, A. et al. *J. Biol. Chem.* 265: 10226–10231 (1990); Chen, K. S. et al. *Trans. Assoc. Am. Physicians* 104: 206–212 (1991); Chin, J. E. et al. *J. Biol. Chem.* 268: 6338–6347 (1993). In addition, studies have demonstrated a marked increase in protein kinase C activity in tissues known to be susceptible to diabetic complications when exposed to hyperglycemic conditions. Lee, T. S. et al. *J. Clin. Invest.* 83: 90–94 (1989); Lee, T, S. et al. *Proc. Natl. Acad. Sci. USA* 86: 5141–5145 (1989); Craven, P. A. and DeRubertis, F. R. *J. Clin. Invest.* 83: 1667–1675 (1989); Wolf, B. A. et al. *J. Clin. Invest.* 87: 31–38 (1991); Tesfamariam, B. et al. *J. Clin. Invest.* 87: 1643–1648 (1991).

The compounds of Formula I are preferably formulated prior to administration. Therefore, yet another embodiment of the present invention is a pharmaceutical formulation comprising a compound of Formula I and one or more pharmaceutically acceptable carriers, diluents or excipients.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 1 to about 500 mg, more typically about 5 to about 300 mg, of the active ingredient. However, it will be understood that the therapeutic dosage administered will be determined by the physician in the light of the relevant circumstances including the condition to be treated, the choice of compound to be administered and the chosen route of administration. Therefore the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, the compounds of the present invention may be administered topically. Topical formulations are ointments, creams, and gels. Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added to an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should only be a range sufficient to permit ready application of the formulation to the an affected tissue area in an amount which will deliver the desired amount of compound.

The customary amount of a topical formulation to be applied to an affected tissue will depend upon an affected tissue size and concentration of compound in the formulation. Generally, the formulation will be applied to the effected tissue in an amount affording from about 1 to about 500 $\mu$g compound per $cm^2$ of an affected tissue. Preferably, the applied amount of compound will range from about 30 to about 300 $\mu g/cm^2$, more preferably, from about 50 to about 200 $\mu g/cm^2$, and, most preferably, from about 60 to about 100 $\mu g/cm^2$.

The following formulation examples are illustrative only and are not intended to limit the scope of the invention in anyway.

Formulation 1

Hard gelatin capsules are prepared using the following ingredients:

| | Quantity (mg/capsule) |
|---|---|
| Active agent | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/capsule) |
|---|---|
| Active agent | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

| | Quantity (mg/capsule) |
|---|---|
| Active agent | .025 |
| ethanol | 29.75 |
| Propellant 22 (chlorodifluoromethane) | 70.00 |
| Total | 100.00 |

The active compound is mixed with ethanol. The mixture is added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| | Quantity (mg/capsule) |
|---|---|
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | Quantity (mg/capsule) |
|---|---|
| Active agent | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| | Quantity (mg/capsule) |
|---|---|
| Active agent | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 mL dose are made as follows:

| | Quantity (mg/capsule) |
|---|---|
| Active agent | 50 mg |
| sodium carboxymethyl cellulose | 50 mg |
| syrup | 1.25 mg |
| benzoic acid solution | 0.10 mg |
| flavor | q.v. |
| color | q.v. |
| purified water to total | 5 mL |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | Quantity (mg/capsule) |
|---|---|
| Active agent | 250 mg |
| isotonic saline | 1,000 mg |

The solution of the above ingredients is administered intravenously at a rate of 1 mL per minute to a subject in need of treatment.

We claim:

1. A compound of the formula:

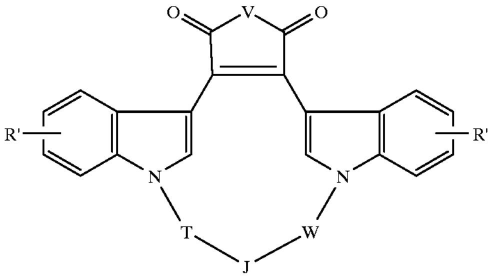

wherein;

R' is independently hydrogen, halo, hydroxy, $C_1$–$C_4$ alkyl, $C_1$–$C_4$ alkoxy, $NR_3R_4$ or —NHCO($C_1$–$C_4$ alkyl);

V is —O—, —NH— or —$NC_1$–$C_4$ alkyl—;

T is $C_1$–$C_4$ alkylene unsubstituted or substituted with halo or $C_1$–$C_4$ alkyl;

W is $C_1$–$C_2$ alkylene unsubstituted or substituted with halo or $C_1$–$C_4$ alkyl;

J is

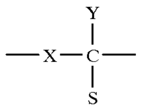

or when T and W are both methylene, J is selected from the group consisting of

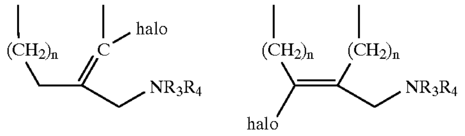

and

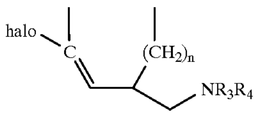

wherein n and m are independently 1 or 2;

X is oxygen, sulfur or a bond between the carbon atom bridged by X;

Y is halo, $C_1$–$C_4$ alkyl or hydrogen;

S is —CHO or the group

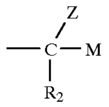

wherein M is hydrogen, —$CH_2OR_5$, —$CH_2NR_3R_4$ or —$NR_3R_4$;

$R_2$ is hydrogen or halo; and

Z is hydrogen or —$OR_6$;

wherein $R_3$ and $R_4$ are independently hydrogen, $C_1$–$C_4$ alkyl, $C_1$–$C_4$ alkanoyl or halo($C_1$–$C_4$ alkanoyl) or $R_3$ and $R_4$ taken together with the N atom to which they are bound form a 5 or 6-membered ring; and $R_5$ and $R_6$ are independently hydrogen, $C_1$–$C_4$ alkyl, $C_{1-C4}$ alkanoyl or halo($C_1$–$C_4$ alkanoyl) or together form a divalent group of the formula —$CR_7R_8$— wherein $R_7$ and $R_8$ are independently hydrogen or $C_1$–$C_4$ alkyl or $R_7$ and $R_8$ taken together with the C atom to which they are bound form a 5 or 6-membered ring provided that at least one of Y, S, T or W is halo or a halo substituted group, or T and W are both methylene.

2. The compound of claim 1 wherein at least one of Y, S, T or W is fluoro or a fluoro substituted group.

3. A compound of the formula:

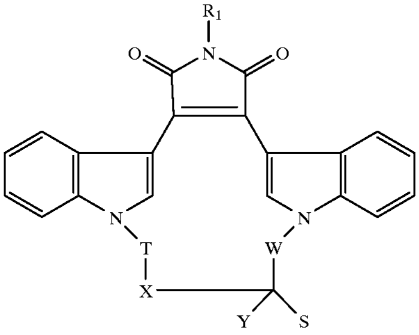

wherein;

$R_1$ is $C_1$–$C_4$ alkyl or hydrogen;

T is $C_2$–$C_4$ alkylene unsubstituted or substituted with halo or $C_1$–$C_4$ alkyl;

W is ethylene unsubstituted or substituted with halo or $C_1$–$C_4$ alkyl;

X is oxygen, sulfur or a bond between the carbon atom bridged by X;

Y is halo, $C_1$–$C_4$ alkyl or hydrogen;

S is —CHO or the group

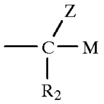

wherein M is hydrogen, —$CH_2OR_5$, —$CH_2NR_3R_4$ or —$NR_3R_4$;

$R_2$ is hydrogen or halo; and

Z is hydrogen or —$OR_6$;

wherein $R_3$ and $R_4$ are independently hydrogen, $C_1$–$C_4$ alkyl, $C_1$–$C_4$ alkanoyl or halo($C_1$–$C_4$ alkanoyl) or $R_3$ and $R_4$ taken together with the N atom to which they are bound form a 5 or 6-membered ring; and $R_5$ and $R_6$ are independently hydrogen, $C_1$–$C_4$ alkyl, $C_1$–$C_4$ alkanoyl or halo($C_1$–$C_4$ alkanoyl) or together form a divalent group of the formula —$CR_7R_8$— wherein $R_7$ and $R_8$ are independently hydrogen or $C_1$–$C_4$ alkyl or $R_7$ and $R_8$ taken together with the C atom to which they are bound form a 5 or 6-membered ring provided that at least one of Y, S, T or W is halo or a halo substituted group.

4. The compound of claim 3 wherein at least one of Y, S, T or W is fluoro or a fluoro substituted group.

5. The compound of claim 3 wherein W is fluoro substituted ethylene.

6. The compound of claim 3 wherein T is fluoro substituted ethylene.

7. The compound of claim 3 wherein T is fluoro substituted trimethylene.

8. The compound of claim 3 wherein $R_1$ and Y are hydrogen and X is oxygen.

9. The compound of claim 5 wherein $R_1$ and Y are hydrogen, X is oxygen and S is

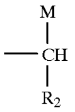

10. The compound of claim 9 wherein T is ethylene.

11. A compound of the formula:

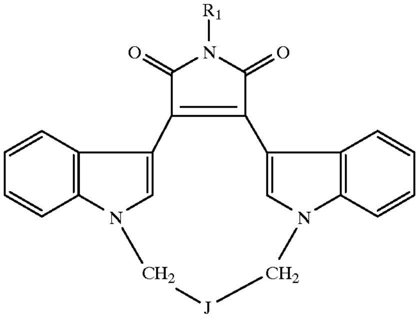

wherein

J is selected from the group consisting of

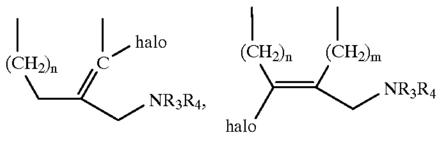

and

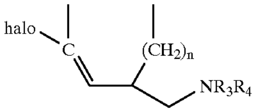

wherein $R_1$ is $C_1$–$C_4$ alkyl or hydrogen;

n and m are independently 1 or 2; and $R_3$ and $R_4$ are independently hydrogen, $C_1$–$C_4$ alkyl, halo($C_1$–$C_4$ alkyl), $C_1$–$C_4$ alkanoyl, halo ($C_1$–$C_4$ alkanoyl) or $R_3$ and $R_4$ taken together with the N atom to which they are bound form a 5 or 6-membered ring.

12. The compound of claim 11 wherein $R_1$ is hydrogen.

13. The compound of claim 11 wherein the halo substituent of J is fluoro.

14. A pharmaceutical composition comprising a compound of the formula:

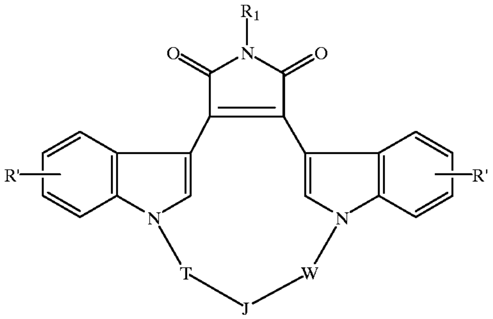

wherein;

R' is independently hydrogen, halo, hydroxy, $C_1$–$C_4$ alkyl, $C_1$–$C_4$ alkoxy, $NR_3R_4$ or —NHCO($C_1$–$C_4$ alkyl);

$R_1$ is $C_1$–$C_4$ alkyl or hydrogen;

T is $C_1$–$C_4$ alkylene unsubstituted or substituted with halo or $C_1$–$C_4$ alkyl;

W is $C_1$–$C_2$ alkylene unsubstituted or substituted with halo or $C_1$–$C_4$ alkyl;

J is

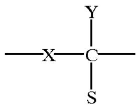

or when T and W are both methylene, J is selected from the group consisting of

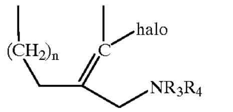

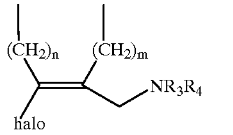

and

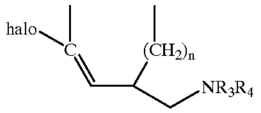

wherein n and m are independently 1 or 2;

X is oxygen, sulfur or a bond between the carbon atom bridged by X;

Y is halo, $C_1$–$C_4$ alkyl or hydrogen;

S is —CHO or the group

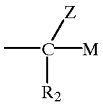

wherein M is hydrogen, —$CH_2OR_5$, —$CH_2NR_3R_4$ or —$NR_3R_4$;

$R_2$ is hydrogen or halo; and

Z is hydrogen or —$OR_6$;

wherein $R_3$ and $R_4$ are independently hydrogen, $C_1$–$C_4$ alkyl, $C_1$–$C_4$ alkanoyl or halo($C_1$–$C_4$ alkanoyl) or $R_3$ and $R_4$ taken together with the N atom to which they are bound form a 5 or 6-membered ring; and $R_5$ and $R_6$ are independently hydrogen, $C_1$–$C_4$ alkyl, $C_1$–$C_4$ alkanoyl or halo($C_1$–$C_4$ alkanoyl) or together form a divalent group of the formula —$CR_7R_8$— wherein $R_7$ and $R_8$ are independently hydrogen or $C_1$–$C_4$ alkyl or $R_7$ and $R_8$ taken together with the C atom to which they are bound form a 5 or 6-membered ring provided that at least one of Y, S, T or W is halo or a halo substituted group, or T and W are both methylene; and a pharmaceutically acceptable excipient, carrier, or diluent.

15. The pharmaceutical composition of claim 14 wherein J is

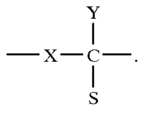

16. The pharmaceutical composition of claim 15 wherein S is

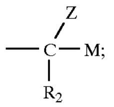

X is oxygen; and $R_1$ is hydrogen.

17. The pharmaceutical composition of claim 16 wherein at least one of Y, S, T or W is fluoro or a fluoro substituted group.

18. The pharmaceutical composition of claim 14 wherein T and W are methylene and the halo substituent is fluoro.

19. A method of treating a mammal having a disease or condition associated with abnormal protein kinase C activity, said method comprising administering to said mammal a pharmaceutically effective amount of compound of the formula:

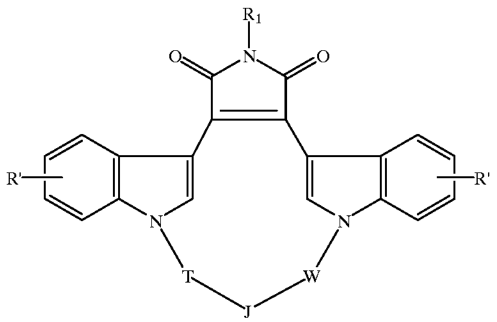

wherein;

R' is independently hydrogen, halo, hydroxy, $C_1$–$C_4$ alkyl, $C_1$–$C_4$ alkoxy, $NR_3R_4$ or —NHCO($C_1$–$C_4$ alkyl);

$R_1$ is $C_1$–$C_4$ alkyl or hydrogen;

T is $C_1$–$C_4$ alkylene unsubstituted or substituted with halo or $C_1$–$C_4$ alkyl;

W is $C_1$–$C_2$ alkylene unsubstituted or substituted with halo or $C_1$–$C_4$ alkyl;

J is

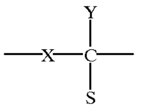

or when T and W are both methylene, J is selected from the group consisting of

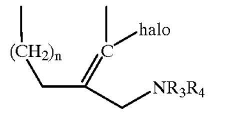

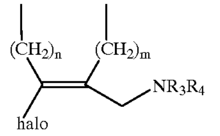

and

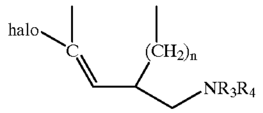

wherein n and m are independently 1 or 2;

X is oxygen, sulfur or a bond between the carbon atom bridged by X;

Y is halo, $C_1$–$C_4$ alkyl or hydrogen;

S is —CHO or the group

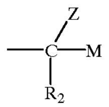

wherein M is hydrogen, —$CH_2OR_5$, —$CH_2NR_3R_4$ or —$NR_3R_4$;

$R_2$ is hydrogen or halo; and

Z is hydrogen or —$OR_6$;

wherein $R_3$ and $R_4$ are independently hydrogen, $C_1$–$C_4$ alkyl, $C_1$–$C_4$ alkanoyl or halo($C_1$–$C_4$ alkanoyl) or $R_3$ and $R_4$ taken together with the N atom to which they are bound form a 5 or 6-membered ring; and $R_5$ and $R_6$ are independently hydrogen, $C_1$–$C_4$ alkyl, $C_1$–$C_4$ alkanoyl or halo($C_1$–$C_4$ alkanoyl) or together form a divalent group of the formula —$CR_7R_8$— wherein $R_7$ and $R_8$ are independently hydrogen or $C_1$–$C_4$ alkyl or $R_7$ and $R_8$ taken together with the C atom to which they are bound form a 5 or 6-membered ring provided that at least one of Y, S, T or W is halo or a halo substituted group, or T and W are both methylene; and a pharmaceutically acceptable excipient, carrier, or diluent.

20. The method of claim 19 wherein

J is

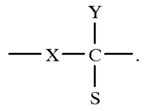

21. The method of claim 20 wherein

S is

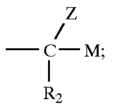

X is oxygen; and $R_1$ is hydrogen.

22. The method of claim 20 wherein at least one of Y, S, T or W is fluoro or a fluoro substituted group.

23. The method of claim 19 wherein

T and W are methylene and the halo substituent is fluoro.

24. The method of claim 19 wherein W is fluoro substituted ethylene.

25. The method of claim 19 wherein T is fluoro substituted ethylene.

26. The method of claim 19 wherein T is fluoro substituted trimethylene.

* * * * *

UNITED STATES PATENT AND TRADEMARK OFFICE

CERTIFICATE OF CORRECTION

PATENT NO. : 5,936,084

DATED : August 10, 1999

INVENTOR(S) : Michael R. Jirousek et al.

It is certified that error appears in the above-identified patent and that said Letters Patent is hereby corrected as shown below:

<u>Column 72,</u>

The second chemical structure please correct

" 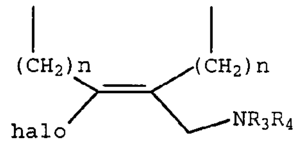 " to read -- 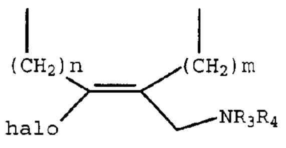 --.

Line 57, please correct “$C_{1-C4}$” to read -- $C_1$-$C_4$ --.

Signed and Sealed this

Sixth Day of May, 2003

JAMES E. ROGAN

*Director of the United States Patent and Trademark Office*